US011717497B2

(12) United States Patent
Alonso et al.

(10) Patent No.: US 11,717,497 B2
(45) Date of Patent: *Aug. 8, 2023

(54) INDUCED EXPRESSION OF BRAIN DERIVED NEUROTROPHIC FACTOR (BDNF) FOR TREATMENT OF NEUROMUSCULAR, NEURODEGENERATIVE, AUTOIMMUNE, DEVELOPMENTAL AND/OR METABOLIC DISEASES

(71) Applicant: Mitochon Pharmaceuticals, Inc., Blue Bell, PA (US)

(72) Inventors: Robert Alonso, North Hampton, NH (US); John Gerard Geisler, Blue Bell, PA (US)

(73) Assignee: Mitochon Pharmaceuticals, Inc., Blue Bell, PA (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/093,193

(22) Filed: Nov. 9, 2020

(65) Prior Publication Data

US 2021/0052513 A1 Feb. 25, 2021

Related U.S. Application Data

(63) Continuation of application No. 16/250,470, filed on Jan. 17, 2019, now Pat. No. 10,864,173, which is a continuation of application No. 15/707,239, filed on Sep. 18, 2017, now Pat. No. 10,220,006, which is a continuation of application No. 15/002,531, filed on Jan. 21, 2016, now Pat. No. 9,763,896.

(60) Provisional application No. 62/106,365, filed on Jan. 22, 2015.

(51) Int. Cl.
*A61K 31/06* (2006.01)
*A61K 9/00* (2006.01)

(52) U.S. Cl.
CPC ............ *A61K 31/06* (2013.01); *A61K 9/0019* (2013.01); *A61K 9/0053* (2013.01)

(58) Field of Classification Search
CPC ..................................................... A61K 31/06
See application file for complete search history.

(56) References Cited

U.S. PATENT DOCUMENTS

| 6,664,297 | B1 | 12/2003 | Ferreira et al. |
| 7,799,782 | B2 | 9/2010 | Munson et al. |
| 9,763,896 | B2 | 9/2017 | Alonso et al. |
| 9,974,755 | B2* | 5/2018 | Alonso .............. A61P 21/00 |
| 10,220,006 | B2* | 3/2019 | Alonso .............. A61K 9/0053 |
| 10,864,173 | B2* | 12/2020 | Alonso .............. A61P 3/00 |
| 2010/0130597 | A1 | 5/2010 | Chung et al. |

FOREIGN PATENT DOCUMENTS

WO 2015031756 A1 3/2015

OTHER PUBLICATIONS

Chinese Office Action for Chinese Patent Application No. 201680017379.4; dated Dec. 18, 2019; 25 pages.
Japanese Patent Application No. 2017-539363, Official Action dated Nov. 6, 2019.
English translation for Japanese Patent Application No. 2017-539363, Official Action dated Nov. 6, 2019.
Caldeira da Silva et al., "Mild mitochondrial uncoupling in mice affects energy metabolism, redox balance and longevity", Aging Cell, vol. 7, pp. 552-560 (2008).
DeFelice et al., "Inhibition of Alzheimer's disease β-amyloid aggregation, neurotoxicity, and in vivo deposition by nitrophenols: implications for Alzheimer's therapy", The FASEB Journal express article, 15 pages, XP007908887 (Mar. 20, 2001).
DeFelice et al., "Novel Neuroprotective, Neuritogenic and Anti-amyloidogenic Properties of 2,4-Dinitrophenol: The Gentle Face of Janus", IUBMB Life, vol. 58, No. 4, pp. 185-191 (Apr. 1, 2006).
Jin et al., "The Mitochondrial Uncoupling Agent 2,4-Dinitrophenol Improves Mitochondrial Function, Attenuates Oxidative Damage, and Increases White Matter Sparing in the Contused Spinal Cord", Journal of Neurotrauma, vol. 21, No. 10, pp. 1396-1404 (2004).
Korde et al., "The mitochondrial uncoupler 2,4-dinitrophenol attenuates tissue damage and improves mitochondrial homeostasis following transient focal cerebral ischemia", Journal of Neurochemistry, vol. 94, pp. 1676-1684 (2005).

(Continued)

*Primary Examiner* — Rei Tsang Shiao
(74) *Attorney, Agent, or Firm* — Morgan, Lewis & Bockius LLP

(57) ABSTRACT

A method of treating a host of neuromuscular, neurodegenerative, developmental, autoimmune and metabolic diseases/disorders related to aging, such as traumatic injury, stroke, Huntington's disease, Epilepsy, Multiple Sclerosis (MS), Lupus, Type-1 and Type-2 diabetes, Maturity Onset Diabetes of the Young (MODY), myasthenia gravis (MG), rheumatoid arthritis (RA), Graves' disease, Guillain-Barré syndrome (GBS), metabolic syndrome, Muscular Dystrophy or Duchenne Muscular Dystrophy (DMD), severe burns, aging, Amyotrophic Lateral Sclerosis (ALS), Friedreich's Ataxia, Batten Disease, Alzheimer's disease, optic neuritis, Leber's hereditary optic neuropathy (LHON), autism, Rett syndrome, Batten Disease, Angelman's Syndrome, Leigh disease, Fragile-X Syndrome, depression, Parkinson's disease, mitochondrial diseases, developmental disorders, metabolic disease disorders and/or autoimmune disorders by inducing endogenous BDNF expression with DNP treatment to protect from neuromuscular dysfunction/disorders and/or neurodegeneration and/or muscle wasting. DNP was administered to mice daily over a range of doses, and subsequently BDNF expression in the brain showed a dose dependent and non-linear increase in expression.

23 Claims, 12 Drawing Sheets

(56) References Cited

OTHER PUBLICATIONS

Liu, "Integrative adapative responses to mild mitochondrial uncoupling emphasize arc/arg3. 1 signaling and tsc2-associated mtor inhibition", Abstract—Neuroscience 2012, 4 pages.
Liu et al., "The mitochondrial uncoupler DNP triggers brain cell mTOR signaling network reprogramming and CREB pathway up-regulation", Journal of Neurochemistry, vol. 134, pp. 677-692 (2015).
Madeiro da Costa et al., "2,4-Dintrophenol Blocks Neurodegeneration and Preserves Sciatic Nerve Function after Trauma", Journal of Neurotrauma, vol. 27, pp. 829-841 (May 2010).
Pandya et al., "Post-Injury Administration of Mitochondrial Uncouplers Increases Tissue Sparing and Improves Behavioral Outcome following Traumatic Brain Injury in Rodents", Journal of Neurotrauma. Vol. 24, No. 5, pp. 798-811 (Nov. 5, 2007).
Urushitani et al., "N-Methyl-d-Aspartate Receptor-Mediated Mitochondrial Ca2+ Overload in Acute Excitotoxic Motor Neuron Death: A Mechanism Distinct from Chronic Neurotoxicity After Ca2+ Influx", Journal of Neuroscience Research, vol. 63, pp. 377-387 (2001).
Written Opinion for PCT/US2016/014312 dated Mar. 30, 2016.
International Search Report for PCT/US2016/014312 dated Mar. 30, 2016.
International Preliminary Report on Patentability for PCT/US2016/014312 dated Aug. 3, 2017, 10 pages.
Examination Report for EP Patent Application No. 16703409.9 dated Aug. 26, 2019.
Examination report dated Jun. 17, 2020 for Australian Patent Application No. 2016209255.
Second Office Action dated Jul. 13, 2020 for Chinese Patent Application No. 201680017379.4.
Official Action dated Jul. 14, 2020 for Mexican Patent Application No. MX/a/2017/009402.
Eighmyetal CAS: 120:253011, 1994.
Examination report dated Jun. 8, 2020 for European Patent Application No. 16703409.9.
Office action dated May 26, 2021 for Australian Patent Application No. 2016209255.
Office action dated Jul. 20, 2021 for Mexican Patent Application No. MX/a/2017/009402.
Office action dated Nov. 25, 2021 for Mexican Patent Application No. MX/a/2017/009402.
Office action dated Jan. 19, 2021 for Mexican Patent Application No. MX/a/2017/009402.
Office action dated Oct. 15, 2020 for Brazil Patent Application No. 1120170157217.
Agnati, L.F. et al. (2013). A New Interpretative Paradigm for Conformational Protein Diseases. Current Protein and Peptide Science, 14(1): 1-20.
Kang, S. et al. (2009). Secondary Amyloidosis Associated with Multiple Sclerosis. J. Clin. Neurol., 5: 146-148.
Nennesmo, I. et al. (1997). Multiple sclerosis and amyloid deposits in the white matter of the brain. Acta Neuropathol., 93:205-209.
Office action dated Oct. 26, 2020 for Japanese Patent Application No. 2017-539363.
Office action dated Dec. 2, 2020 for Chinese Patent Application No. 201680017379.4.
Office action dated Jul. 9, 2021 for Japanese Patent Application No. 2017-539363.
Office action dated Mar. 24, 2022, in connection with Chinese Patent Application No. 201680017379.4; 15 pages.
Office action dated Apr. 5, 2022, in connection with Canadian Patent Application No. 2,974,092; 6 pages.
Office action dated Dec. 12, 2022, in connection with Canadian Patent Application No. 2,974,092; 6 pages.
Office action dated Oct. 28, 2022, in connection with Japanese Patent Application No. 2021-031635; 11 pages.
Korean Office Action for related Korean Patent Application No. 10-2017-7023034, dated Mar. 24, 2023, 7 pages.
Zhang and Zhang, "iPSCs and small molecules: a reciprocal effort towards better approaches for drug discovery," Acta Pharmacologica Sinica 34:765-776 (2013).
Office Action for related Brazilian Patent Application No. BR112017015721-7, dated Apr. 11, 2023, 4 pages.

\* cited by examiner

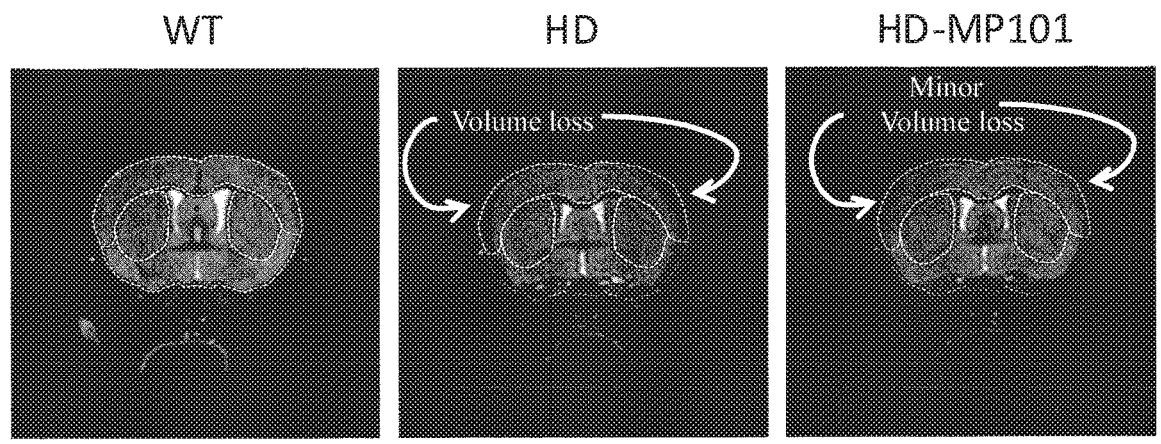
Figure 8a
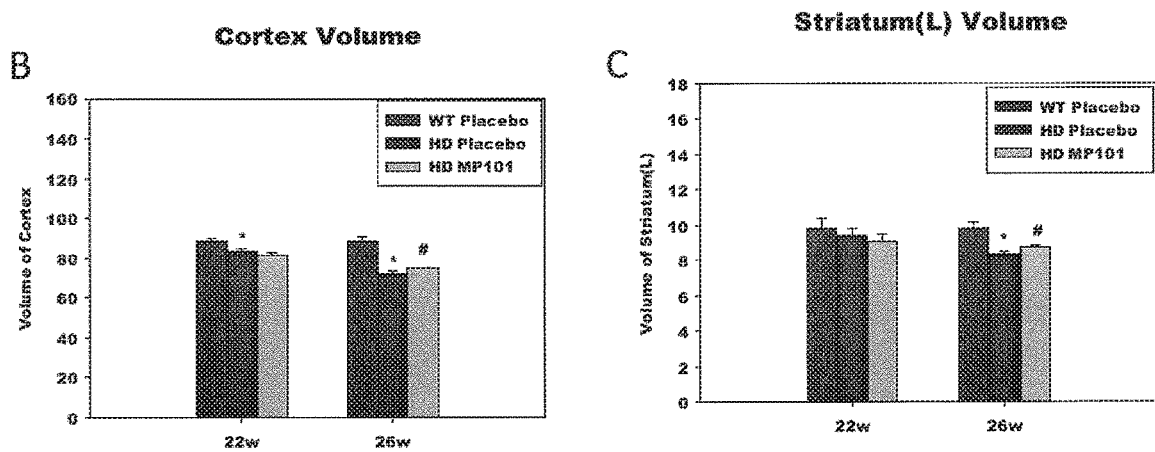
Figure 8b
Figure 8c

INDUCED EXPRESSION OF BRAIN DERIVED NEUROTROPHIC FACTOR (BDNF) FOR TREATMENT OF NEUROMUSCULAR, NEURODEGENERATIVE, AUTOIMMUNE, DEVELOPMENTAL AND/OR METABOLIC DISEASES

CROSS-REFERENCE TO RELATED APPLICATIONS

The present application is a continuation of U.S. application Ser. No. 16/250,470, filed Jan. 17, 2019, now allowed, which is a continuation of U.S. application Ser. No. 15/707,239, filed Sep. 18, 2017, and issued as U.S. Pat. No. 10,220,006 on Mar. 5, 2019, which is a continuation of U.S. application Ser. No. 15/002,531 filed Jan. 21, 2016, and issued as U.S. Pat. No. 9,763,896 on Sep. 19, 2017, which claims the benefit of U.S. Provisional Application Ser. No. 62/106,365 filed Jan. 22, 2015, all of which are incorporated herein by reference in their entireties.

BACKGROUND OF THE INVENTION

Brain-derived neurotrophic factor (BDNF) is one of several endogenous proteins that play key roles in neuronal development. BDNF influences nerve growth as a neurotrophin and/or as a myokine. Therefore there is a need for improved methods for inducing expression of BDNF. The present invention relates to the discovery that BDNF can be endogenously induced to increase expression by administration of DNP, and that there is a dose range between 0.001 mg/kg to less than 10 mg/kg that is useful in expression of BDNF and not harmful to the patient. Further, many approaches are underway to get BDNF across the blood brain barrier to treat a host of diseases. For example, these diseases include, but are not limited to, traumatic injury, stroke, Huntington's disease, Epilepsy, Multiple Sclerosis (MS), Lupus, Type-1 and Type-2 diabetes, Maturity Onset Diabetes of the Young (MODY), Myasthenia gravis (MG), rheumatoid arthritis (RA), Graves' disease, Guillain-Barré syndrome (GBS), metabolic syndrome, Duchenne Muscular Dystrophy (DMD), severe burns, aging, Amyotrophic Lateral Sclerosis (ALS), Friedreich's Ataxia, Batten Disease, Alzheimer's disease, Optic neuritis, Leber's hereditary optic neuropathy (LHON), Autism, Rett syndrome, Batten Disease, Angelman's Syndrome, Leigh disease, Fragile-X Syndrome, Schizophrenia, Depression, Parkinson's disease and mitochondrial diseases. Treatment works by the process of reversing, slowing or preventing neuromuscular, neurodegenerative, autoimmune, developmental and/or metabolic disorders.

FIELD OF THE INVENTION

The present invention relates to methods of treatment of neuromuscular, neurodegenerative, autoimmune, developmental and/or metabolic disease and pharmaceutical compositions, including unit doses, for treatment of neuromuscular, neurodegenerative, autoimmune, developmental and/or metabolic disease. Specifically, the present invention relates to endogenously inducing the systemic organs of a person to increase expression of brain derived neurotrophin factor ("BDNF") via administering mitochondrial uncoupler (protonophore or ionophore) 2, 4-dinitrophenol ("DNP") or bipartite dinitrophenol isoforms (2,3-, 2,4-, 2,5-, 2,6-, 3,4-, or 3,5-DNP) or mitochondrial uncouplers or weak acid's with a dissociable proton such as CCCP, FCCP, SF 6847, Flufenamic acid, PCP, TTFB, etc., to a patient in need thereof, using an effective dose of about 0.001 mg/kg to 5 mg/kg, as well as the associated pharmaceutical composition of DNP and unit dose of DNP.

BRIEF SUMMARY OF THE INVENTION

In one embodiment, the present invention provides for a method of treating traumatic CNS injury, neurodegenerative disease, and/or autoimmune diseases, and/or developmental disorders, and/or metabolic disease by administrating DNP in the dose range of 0.01 mg/kg of body weight to less than 10 mg/kg of body weight to increase BDNF to attenuate disease progression or provide relief from symptoms. In certain embodiments, the invention provides a method of treatment for at least the following diseases: Traumatic Brain Injury (TBI), Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity Onset Diabetes of the Young (MODY: MODY1, MODY2, MODY3, MODY4, MODY5, MODY6, MODY7, MODY8, MODY9, MODY10, MODY11)), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD), Becker, Myotonic, Congenital, Emery-Dreifuss, Facioscapulohumeral, Limbgirdle, Distal, and Oculopharyngeal), severe burns, aging, Amyotrophic Lateral Sclerosis (ALS), Ataxia (Friedreich's Ataxia, Spinocerebellar ataxias 1 (SCA1), Spinocerebellar ataxias 2 (SCA2), Spinocerebellar ataxias 3 (SCA3), Spinocerebellar ataxias 6 (SCA6), Spinocerebellar ataxias 7 (SCA7), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), mitochondrial diseases, developmental disorders, metabolic syndrome (increased blood pressure, high blood sugar level, excess body fat around the waist and abnormal cholesterol levels) and/or autoimmune disorders by inducing BDNF mRNA expression and protein levels with DNP treatment to reverse, slow or prevent neuromuscular and/or neurodegeneration and/or muscle wasting.

In another embodiment, the present invention relates to a composition of DNP, or a pharmaceutically acceptable salt, solvate, or hydrate thereof, comprising an effective dose of DNP, wherein the effective dose of the DNP is in the range of 0.001 mg/kg of body weight to 5 mg/kg of body weight.

In yet another embodiment, the present invention relates to a pharmaceutical composition of DNP, or a pharmaceutically acceptable salt, solvate, or hydrate thereof, comprising a unit dose, wherein the unit dose is in the range of 0.1 mg to 300 mg.

In yet another embodiment, the present invention relates to a method of treating neuromuscular or autoimmune or developmental or neurodegenerative or metabolic disorders, comprising receiving an effective dose of DNP, or a pharmaceutically acceptable salt thereof, over period sufficiently long to achieve remission of the symptoms of the disease, wherein the effective dose of the DNP is continued to be received in the dose range of 0.001 mg/kg of body weight to 5 mg/kg of body weight to increase BDNF to attenuate disease progression or provide remission of symptoms.

A fifth aspect of the present invention relates to a method of treating neuromuscular or autoimmune or developmental or metabolic or neurodegenerative disorders, comprising: providing instructions to administer an effective dose of DNP, or a pharmaceutically acceptable salt thereof, over period sufficiently long to achieve remission of the symptoms of the disease, wherein the effective dose of the DNP is instructed to be received in the dose range of 0.001 mg/kg of body weight to 5 mg/kg of body weight.

BRIEF DESCRIPTION OF THE FIGURES

The present invention will be better understood by examining the following figures which illustrate certain properties of the present invention wherein:

FIG. 8a depicts an MRI image of brain volume changes of wildtype (WT), mutant Huntington mice Vehicle (HD) with DNP treatment.

FIG. 8b depicts the quantitative brain volume loss in the cortex after DNP treatment.

FIG. 8c shows the quantitative brain volume loss in the striatum after DNP treatment.

DETAILED DESCRIPTION OF THE INVENTION

Figure 1:
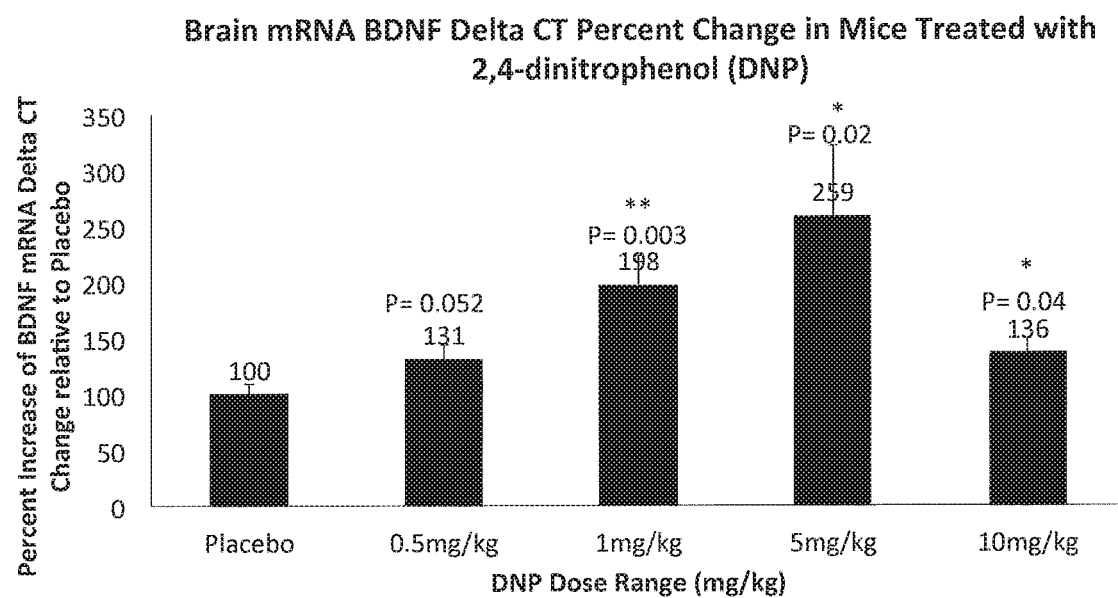
FIG. 1 depicts a chart showing that administration of DNP increases BDNF levels in the brain, in accordance with embodiments of the present invention.

Hereinafter, the term "endogenous", unless otherwise defined, means growing or produced by growth from deep tissue, e.g. by growth from a person's brain. Alternatively, the term "endogenous", unless otherwise defined, means caused by factors inside the organism or system. Alternatively, the term "endogenous", unless otherwise defined, means produced or synthesized within the organism or system.

Hereinafter, unless otherwise defined, the term "muscle wasting" means atrophy of a person's muscle (e.g. diaphragm for breathing). Muscle atrophy is when muscles waste away. The main reason for muscle wasting is a lack of physical activity. This can happen when a disease or injury makes it difficult or impossible for you to move an arm or leg.

Hereinafter, unless otherwise defined, the terms "effective dose" or "effective relief" are measured objectively using one or more of the following quantitative assessments to achieve a validated assessment of the effectiveness of the dose or relief: ADS COG for Alzheimer's Disease; HDRS for Huntington's Disease; the Parkinson Rating Scale for Parkinson's Disease; the FSS and EDSS for Multiple Sclerosis; the ALSAQ for ALS; Stroke Assessment Scales of Stroke such as the NIH Stroke Scale or Barthel Index; Childhood Autism Rating Scale (CARS) for Autism; 6-minute walk test for Duchenne muscular dystrophy (DMD); and a seizure severity scale for seizures.

Hereinafter, unless otherwise defined, the term "about" means plus or minus 10% of the value referenced. For example, "about 1 mg/kg" means 0.9 mg/kg to 1.1 mg/kg.

Mitochondria uncouplers, e.g., 2, 4-dinitrophenol (DNP), may be advantageously administered as a therapeutic approach for neuroprotection in cases of traumatic CNS injury, neurodegenerative disease, autoimmune disease, developmental disorders, and metabolic disease. Mitochondria uncoupling can have a protective effect on brain cells by enhancing respiratory rates by mild uncoupling which leads to lower cellular stress due to a mechanism of action (MOA) of: 1) increasing oxygen ($O_2$) consumption, which prevents formation of superoxide radical anions ($O_2^-$) by decreasing $O_2$ tension in the microenvironment, 2) providing more oxidized levels of respiratory chain intermediates, such as in Complex I and III, known as a substantial source of reactive oxygen species (ROSs), 3) maintaining NADH levels lower, which prevents ROS formation by mitochondrial matrix flavoproteins and 4) lower membrane potential ($\Delta\Psi$), a condition which thermodynamically disfavors reverse of electron transfer from Complex II to I.

Further, neurite outgrowth may, in theory, be achieved with the use of uncouplers beyond the use for lowering ROSs. It is known that DNP can lower ROSs species with an acute single dose post-ischemia, and reduce infarct volume, however the benefits of improved outcome and recovery by repair can be accomplished with increasing expression of BDNF, requiring chronic treatment to induce sufficient levels of this neurotrophin. Infarct volume may therefore be further reduced from repair/growth of the damaged tissue by chronic DNP treatment.

In one embodiment, the present invention relates to the discovery that BDNF can be endogenously induced to increase expression with the treatment of DNP, and that there is a dose range of DNP that is effective and is not too high to be harmful, nor too low and provide no effect. The effectiveness of DNP in inducing BDNF does not increase linearly as the dose of DNP is increased. In one embodiment, we show that there is a DNP dose amount whereby the beneficial effect no longer increases, and, significantly, there is a dose amount whereby the beneficial effect of DNP actually decreases.

While not bound by theory, the mechanism of action for DNP is likely conversion of a non-genomic event into a genomic event. Mitochondrial uncouplers do not directly act upon a protein, but on a location, namely the mitochondrial matrix. The mitochondrial matrix is a pH basic environment due to the pumping out of protons (hydrogen or $H^+$) through the cytochromes. Since mitochondrial uncouplers are weak acids with a dissociable proton, they are attracted to the basic environment of the mitochondrial matrix, where they travel as a cation and drop off a proton ($H^+$), then leave unprotonated back into the acidic environment of cytosol as an anion, to then get reprotonated back to a cation and start the cycle over again until metabolized and/or eliminated. This event lowers the mitochondrial membrane potential, which results in an increase in energy expenditure with the consumption of glucose and lipids in an attempt to re-establish the membrane potential. This effect is considered non-genomic, since DNP does not act directly through a protein or touch a protein, but just goes into a unique location within the cell of which happens to be the only location with a pH basic environment. It also lowers intra-mitochondria calcium. Adenylate cyclase, the enzyme that synthesizes 3'5'-cyclic monophosphate (cyclic AMP or cAMP), otherwise known as "second messenger", is highly sensitive to changes in calcium and magnesium and it has been shown that DNP up-regulates cAMP supplies. The cascade affect of up-regulating adenylate cyclase and producing more cAMP, then converts DNP's non-genomic effect, into a genomic effect, which changes expression of a host of genes, including increasing the transcription factor for BDNF, known as cAMP-responsive element-binding protein (CREB).

By way of example only, BDNF is lower in Huntington's Disease, and restoring BDNF to near normal levels is considered to be critical to attenuate disease onset. Therefore, treatment with DNP that effectively crosses the blood brain barrier and induces endogenous expression of BDNF is advantageous for treating diseases for which increased expression of BDNF will provide neuroprotection. Similarly, Rett Syndrome is considered a developmental disorder in young girls and is associated with lower levels of BDNF. Restoring levels back to near normal levels may prevent the stunting of head growth that appears around approximately 18 months of age as one marker of onset. For other diseases, such as multiple sclerosis (MS), the positive effects of BDNF have not been well studied, but we have shown in a model of MS that BDNF levels are elevated in the brain and striking axonal protection from the autoimmune disorder that destroys the myelin sheaths under chronic treatment of DNP. Others have shown that BDNF can lower glucose levels in models of obesity and diabetes. Others have found that young, non-obese insulin resistant patients have low circulating levels of BDNF, which acts as a paracrine and may be a factor in the metabolic syndrome. Therefore, an elevated and sustained increase in BDNF may provide a broad effect in neurodegeneration, development, autoimmune, metabolic and neuromuscular disorders. In addition, an increase of BDNF in both central and/or peripheral compartments may be beneficial.

In addition to the brain, BDNF is also expressed in other muscle tissues and thought to act as a myokine to provide neuromuscular or muscle protection, in addition to protection from neurodegeneration.

Surprisingly, the dose range of about 0.001 to 5 mg/kg has been shown to be effective in treating muscular, neuromuscular, neurodegenerative, autoimmune, developmental and/or metabolic diseases, such as, for example, traumatic injury, stroke, Huntington's disease, Epilepsy, Multiple Sclerosis (MS), Lupus, Type-1 and Type-2 diabetes, MODY, metabolic syndrome, Duchenne Muscular Dystrophy (DMD), severe burns, aging, Amyotrophic Lateral Sclerosis (ALS), Friedreich's Ataxia, Batten Disease, Alzheimer's disease, Optic neuritis, Autism, Rett syndrome, Batten Disease, Angelman's Syndrome, Fragile-X Syndrome, Schizophrenia, Depression, and Parkinson's disease. In one embodiment, the invention shows use of DNP in the effective dose range of about 0.01 to less than 10 mg/kg to induce expression of BDNF in the brain of mammals, which avoid inducing too much BDNF to be harmful, or have no effect by inducing too little BDNF.

As described herein below, mitochondrial uncoupler DNP was tested in a range of doses in mice from 0.5 mg/kg of DNP to 10 mg/kg of DNP under oral chronic treatment to titrate the amount of drug in the brain required to induce increases of BDNF endogenously within the brain. It was discovered that DNP does in fact induce BDNF within the brain, but the highest dose of 10 mg/kg had a reduced level of BDNF compared with the next two lower doses. Therefore, it was discovered that there is a specific and limited dose range of DNP that is necessary to achieve statistically significant survival and behavioral benefit for a host of diseases that benefit from increased BDNF levels. In one embodiment, diseases and disorders of the systemic organs and brain, islets of Langerhans, liver and brain may benefit from titrating the BDNF levels with a specific and limited DNP dose, such as, but not limited to, Traumatic Brain Injury (TBI), Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity Onset Diabetes of the Young (MODY: MODY1, MODY2, MODY3, MODY4, MODY5, MODY6, MODY7, MODY8, MODY9, MODY10, MODY11)), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD), Becker, Myotonic, Congenital, Emery-Dreifuss, Facioscapulohumeral, Limb-girdle, Distal, and Oculopharyngeal), severe burns, aging, Amyotrophic Lateral Sclerosis (ALS), Ataxia (Friedreich's Ataxia, Spinocerebellar ataxias 1 (SCA11), Spinocerebellar ataxias 2 (SCA2), Spinocerebellar ataxias 3 (SCA3), Spinocerebellar ataxias 6 (SCA6), Spinocerebellar ataxias 7 (SCA7), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), mitochondrial diseases, developmental disorders, metabolic syndrome (increased blood pressure, high blood sugar level, excess body fat around the waist and abnormal cholesterol levels) and/or autoimmune disorders.

Wildtype C57BL/6J mice were treated with 2, 4-dinitrophenol for two weeks daily by oral gavage at 0.5, 1.0, 5.0, and 10.0 mg/kg DNP or placebo, N=8 per group. Brain tissue was used for semi quantitative polymerase chain reaction (PCR) to determine endogenous BDNF levels normalized to GapDH to determine delta-delta CT changes in mRNA. Data shows the delta-delta CT change for each dose level of DNP expressed as a percent change relative to the control group, which was given a placebo.

FIG. 1 shows that administration of DNP in Wildtype Mouse increases BDNF levels in the brain between 0.1 mg/kg DNP and 10 mg/kg DNP, and we have identified a bell-shaped curve such that at the higher dose of 10.0 mg/kg DNP, less BDNF is expressed. In one embodiment, a higher dose range of DNP may benefit patient populations that are in need of higher BDNF levels, such as Huntington's Disease, Rett Syndrome, Epilepsy, and Multiple Sclerosis (MS), and other forms of neurodegeneration and muscle or neuromuscular disorders, since BDNF is a myokine and can provide a positive benefit to muscle wasting.

Figure 2A:
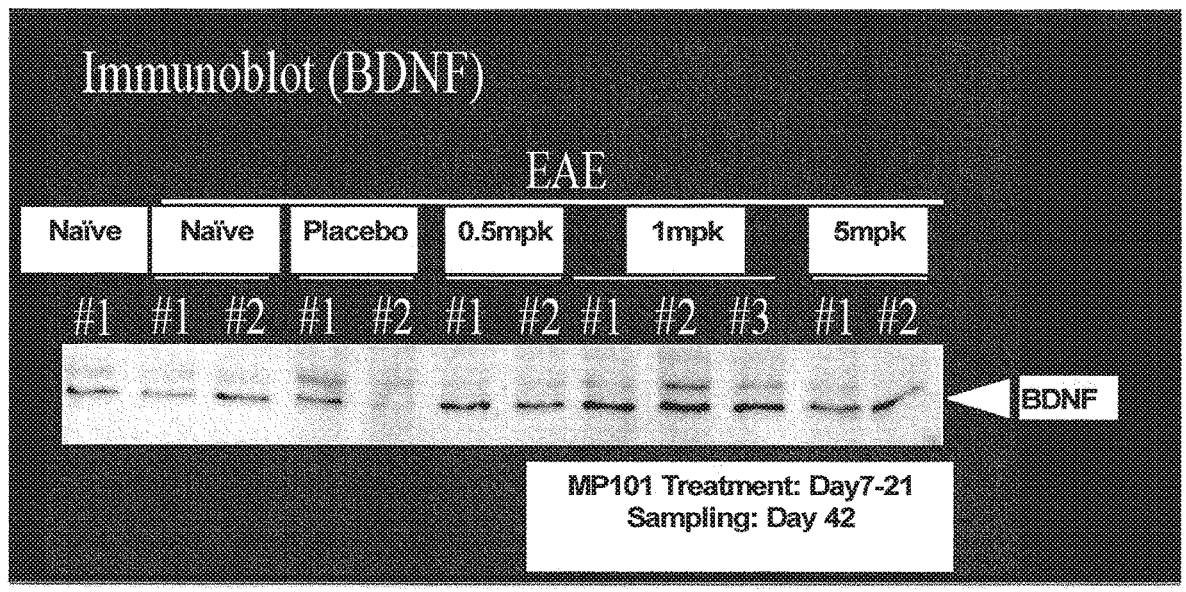
FIG. 2a depicts the changes of BDNF protein levels by immunoblot from a mouse model of MS, Experimental Autoimmune encephalomyelitis.

FIG. 2*a* shows the changes of BDNF protein levels by immunoblot from a mouse model of MS, Experimental Autoimmune Encephalomyelitis (EAE). The tissue was taken on Day 42 of the study during the recovery phase from the lumbal spinal cord of representative mice that were immunized on Day 1 with the MOG peptide, then treated with MP101 starting on Day 7 and stopping on Day 21. Intensity of the BDNF band increases from placebo, to 0.5 mg/kg, to 1 mg/kg, with a plateau effect at 5 mg/kg. Untreated animals are shown as naïve. The changes in BDNF levels are therefore 3-weeks post-treatment with DNP (aka MP101). DNP not only increases BDNF, but the effect of increasing BDNF has a lasting effect that is not obvious until now.

Figure 2B:
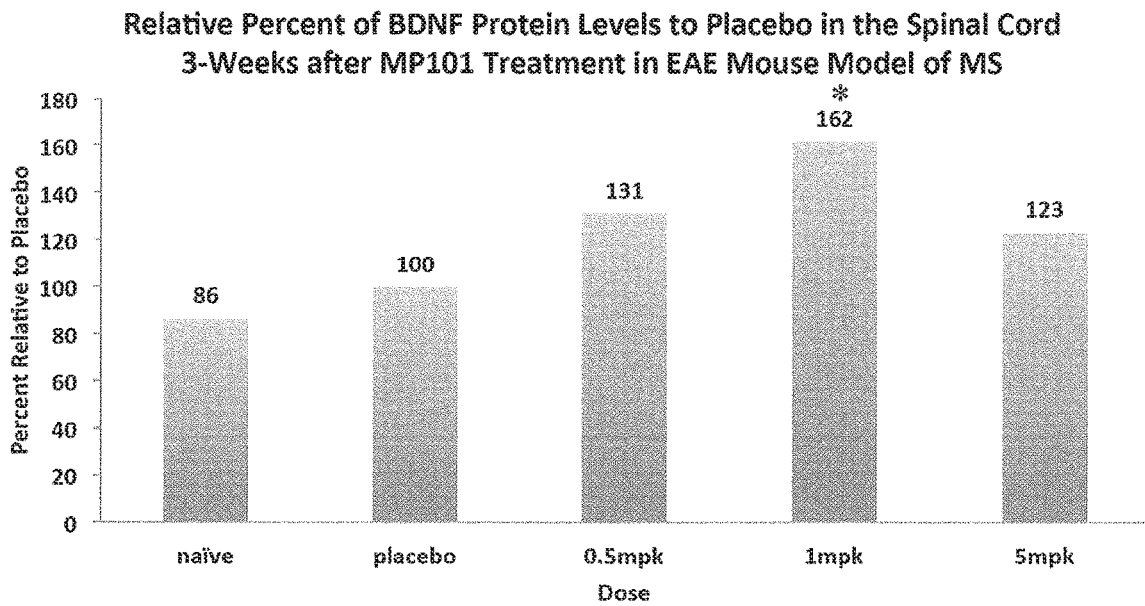
FIG. 2b depicts the percent change of BDNF protein levels from a mouse model of MS based on an immunoblot study.

FIG. 2*b* shows the percent changes of BDNF protein levels by immunoblot from a mouse model of MS, Experimental Autoimmune encephalomyelitis (EAE) 3-weeks post-treatment.

Figure 2C:
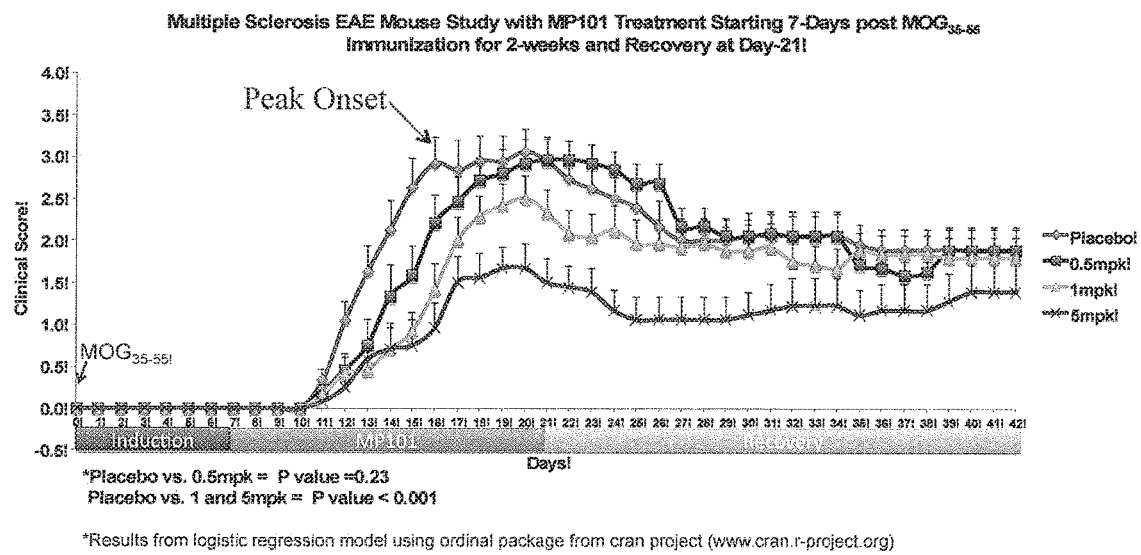
FIG. 2c depicts the effect of MP101 on progression of the phenotype in the MS model on clinical scores showing attenuation of disease progression.

FIG. 2*c* shows the effect of MP101 on progression of the phenotype in the MS model on clinical scores showing attenuation of disease progression.

Figure 2D:
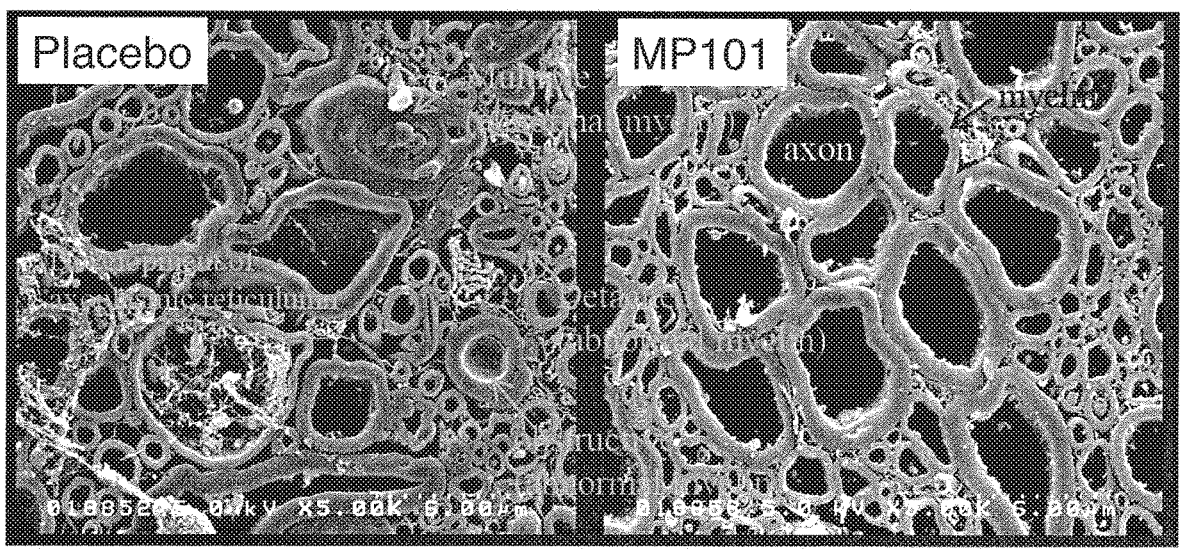
FIG. 2d depicts a representative mouse spinal cord electron microscopy image at Day-16 (~peak of onset) for a mouse treated with 5 mg/kg of MP101 compared to placebo.

FIG. 2*d* shows a representative mouse spinal cord electron microscopy image at Day-16 (~peak of onset) of MP101 5 mg/kg treated mouse compared to placebo. The protective myelin sheaths surrounding the axons and axons are completely intact as compared to the placebo group.

Therefore, we have tested DNP to induce BDNF in the brain of wildtype model by mRNA changes and tested DNP to increase BDNF at the protein level with a demonstration of providing a protective effect in a model of MS, the Experimental Autoimmune Encephalomyelitis (EAE).

MP101 was tested in a model of Rett Syndrome using Mecp2 mutant mice. Rett Syndrome is a developmental disorder in young girls, with first symptoms starting at about 18-months of age, including reduced head growth. FIGS. 3*a*, 3*b*, 3*c* and 4 show the effects of treating these mutant mice with MP101 at 0.5, 1 mg/kg and 5 mg/kg by oral gavage.

Figure 3A:
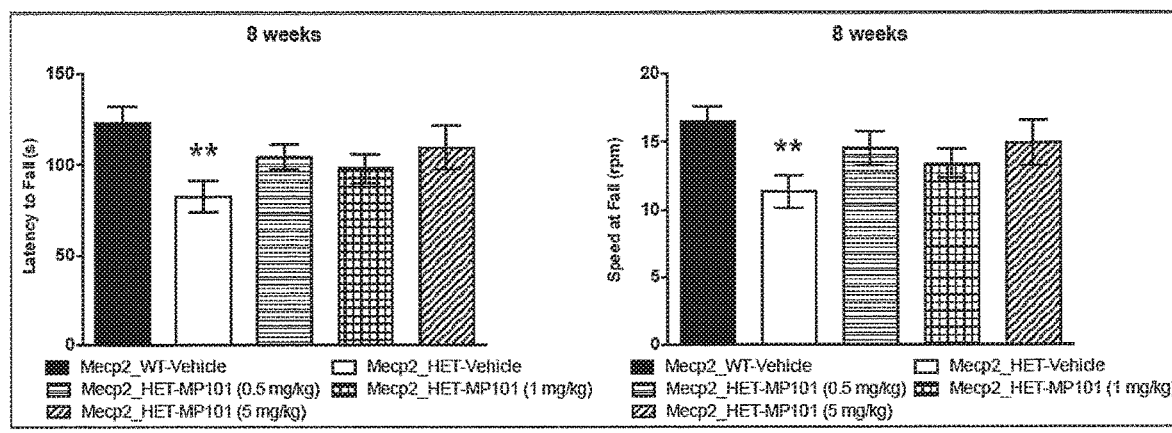
FIG. 3a depicts the results of a study involving Mecp2 mutant mice, a model of Rett Syndrome, after treatment with DNP at 6-weeks of age.
Figure 3B:
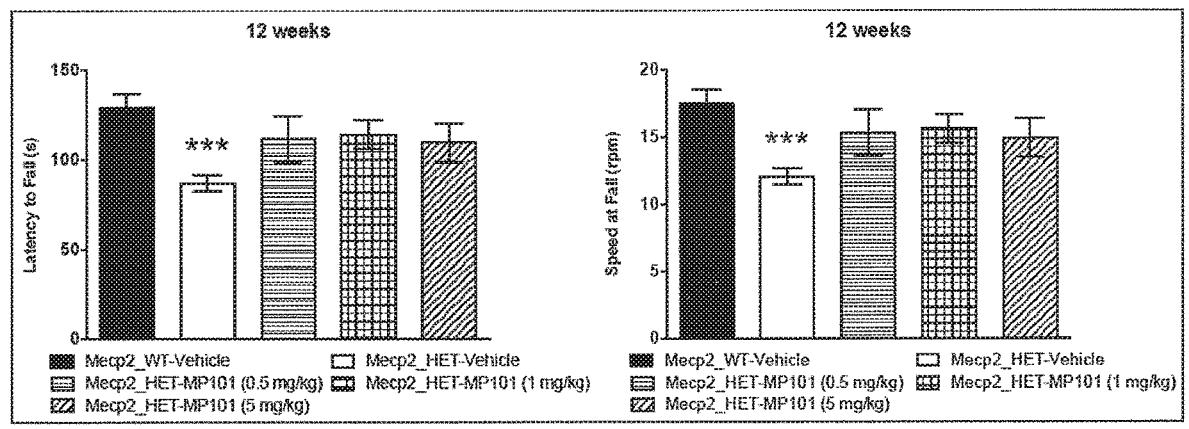
FIG. 3b depicts the results of a study involving Mecp2 mutant mice, a model of Rett Syndrome, after treatment with DNP at 12-weeks of age.

In FIGS. 3*a* and 3*b*, Mecp2 mutant mice, a model of Rett Syndrome, were treated with MP101 (DNP) at 6-weeks of age and tested on their coordination to walk on a rotating cylinder (rotarod). Wildtype mice are used as a benchmark for general decline in behavior compared to Mecp2 mutant mice treated with Vehicle, 0.5 mg/kg MP101, 1 mg/kg MP101 and 5 mg/kg MP101 by oral gavage. In FIG. 3*a*, the data shows that at 8-weeks of age, the mutant vehicle treated mice lost their ability to walk on the rotarod, whereas the wildtype mice and drug treated animals fall less and can handle higher speeds of rotation. In FIG. 3*b*, the data shows similar findings at Week-12 of age after 1-month of treatment.

Figure 4:
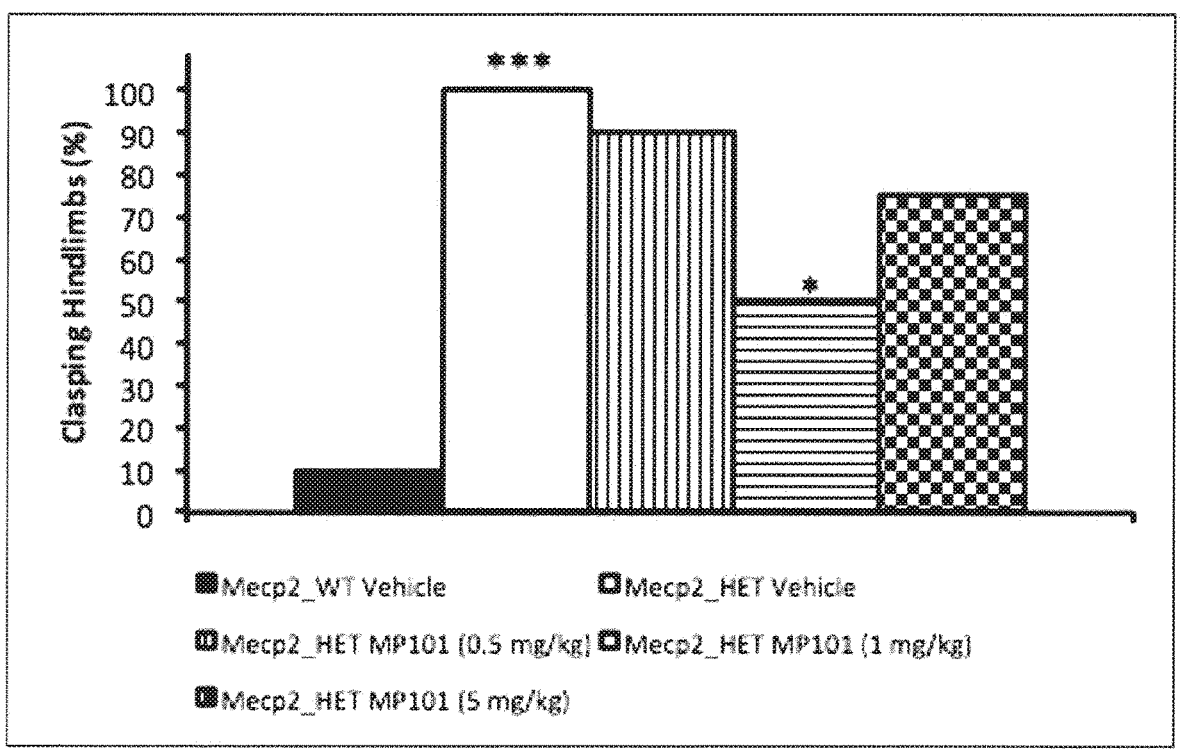
FIG. 4 depicts the results of a study involving Mecp2 mutant mice at 12-weeks of age after 1-month of oral gavage treatment, which shows an effect in the "clasping test" at 1 mg/kg DNP.

In FIG. 4, we show the results of Mecp2 mutant mice at 12-weeks of age and after 1-month of oral gavage treatment, which shows an effect in the "clasping test" at 1 mg/kg MP101.

Figure 5A:
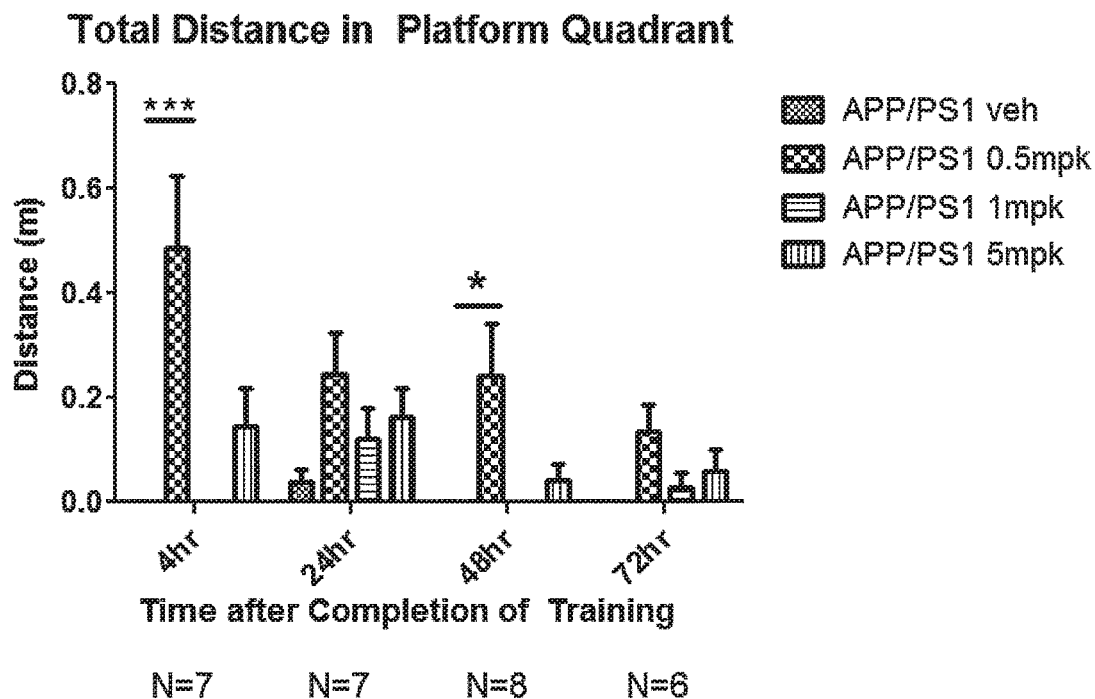
FIGS. 5a, 5b and 5c depict the results of a study involving APP/PS1 mice at 4-months of age after 4-months treatment by oral gavage delivery with DNP in an Alzheimer's study
Figure 5B:
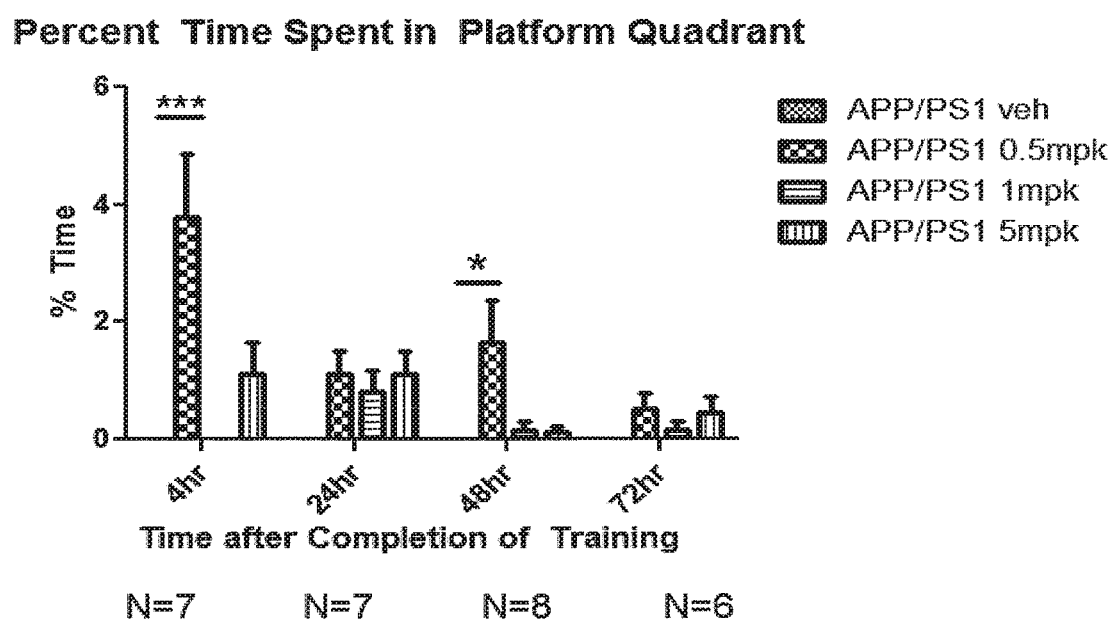
Figure 5C:
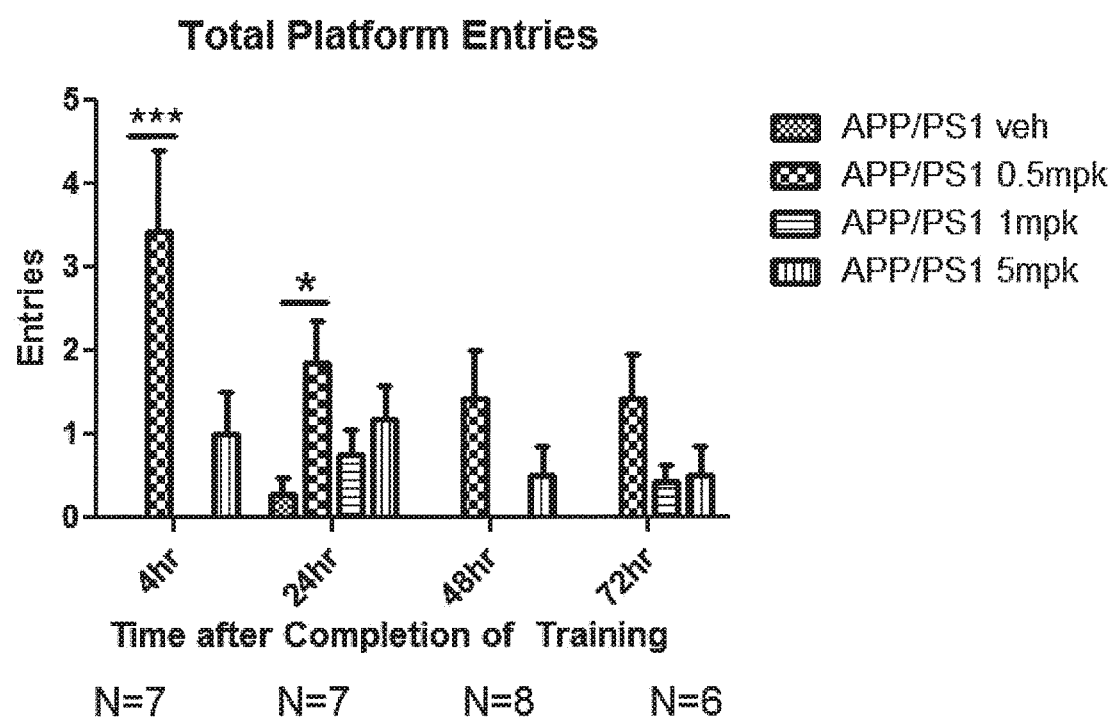

In addition, Alzheimer's Disease, representing about 70% of all dementia cases, was evaluated using the APP/PS1 mice, which express the APPswe mutation and PS1deltaE9 mutation and develop relatively rapid Aβ pathology and cognitive deficits. At 4-months of age, the APP/PS1 mice were treated for 4-months by oral gavage delivery with MP101 (DNP) at 0.5, 1 and 5 mg/kg. FIGS. 5a, 5b and 5c show that MP101 have improved cognition compared to Vehicle treated mice. The amount of time spent in the quadrant is an indicator of whether the mice remember the general location, with increased time indicating increased memory.

FIGS. 5a, 5b and 5c show that at all doses with DNP, the APP/PS1 mice improved in short term memory when tested on the Morris Water Maze for cognition in remembering where the hidden platform was, relative to vehicle which could not. FIG. 5a shows the distance traveled looking for the platform in the quadrant with the hidden platform, FIG. 5b shows the amount of time spent in the quadrant where the platform is hidden, and FIG. 5c shows the number of entries from the platform. The amount of time spent in the quadrant is an indicator of whether the subject remembers the general location.

Figure 6:
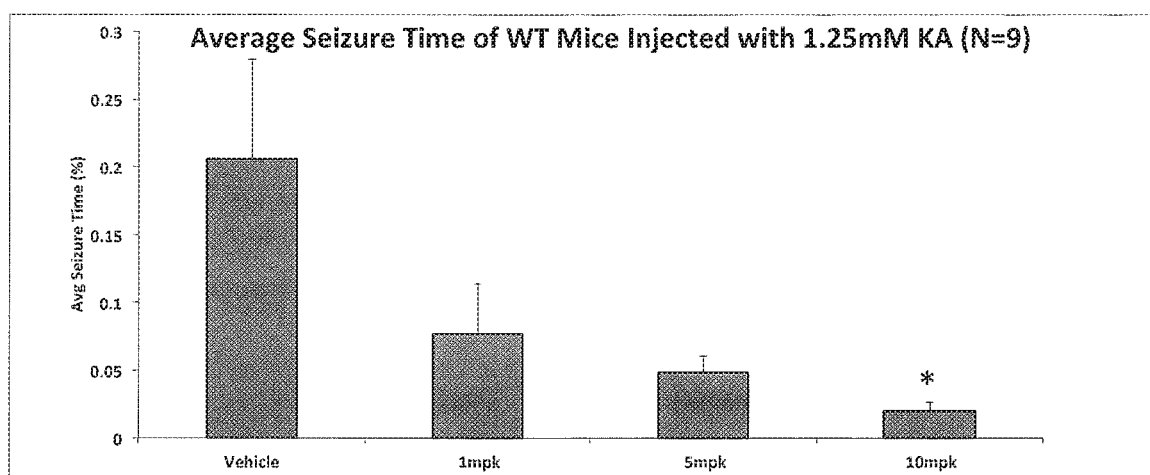
FIG. 6 depicts the results of a mouse study whereby mice were treated with DNP for 2-weeks at 1, 5 and 10 mg/kg by oral gavage and then provide a kanic acid injection into the brain to determine the impact on seizure time.

DNP was also evaluated for a treatment of Epilepsy. The kanic acid model is an acute model of epilepsy caused by an injection in the right hippocampus of an analogue of glutamate (kanic acid) that over-stimulates the neurons causing death. FIG. 6 shows the effect of treating wildtype mice for 14-days by oral gavage at 1, 5 and 10 mg/kg with MP101 (DNP), prior to injection of kanic acid to determine if DNP as a protective effect to the effects on over-stimulation and death by kanic acid.

FIG. 6 shows that after 2-weeks of treatment with MP101 (DNP) at 1, 5 and 10 mg/kg by oral gavage and then a kanic acid injection into the brain of a mouse, there is a shortening of seizure time. DNP provided neural protection from over-stimulation caused by kanic acid relative to the Vehicle.

The merits of treating Parkinson's Disease with MP101 (DNP) was evaluated in wildtype mice and SIRT3 KO mice with 6-OHDA injections after two weeks of MP101 treatment. We examined the neuroprotective effects of varying MP-101 doses (0.5, 1, 5 mg/kg) against dopaminergic degeneration of nigrostriatal neurons induced by a single unilateral stereotaxic injection of neurotoxin 6-hydroxydopamine (6-OHDA) in the right striatum of the brain of 2-3 month old male C57Bl/6 mice or SIRT3 KO mice. SIRT3 KO is a model of a heightened sensitivity to glutamate-induced calcium overload and excitotoxicity, and oxidative and mitochondrial stress, therefore ideal for evaluating Parkinson's Disease, Huntington's Disease and temporal lobe epilepsy. FIG. 7 shows that MP101 protected the dopaminergic neurons from the toxic effects of 6-OHDA.

Figure 7A:
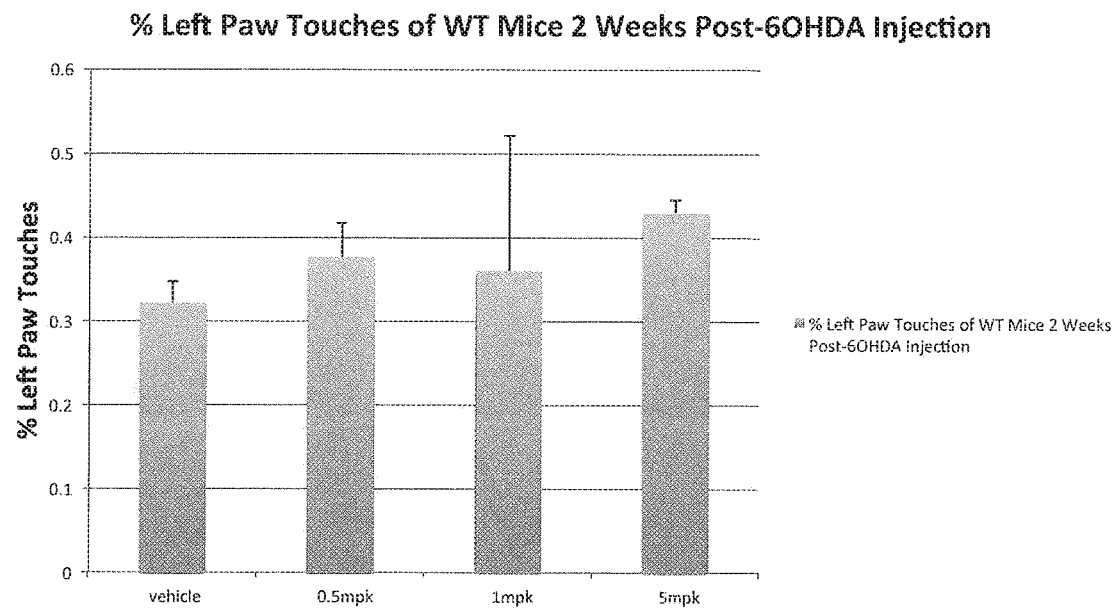
FIG. 7a depicts the results of a mouse study whereby mice were treated with DNP for 14 days to see the impact on protecting dopaminergic neuronal loss.
Figure 7B:
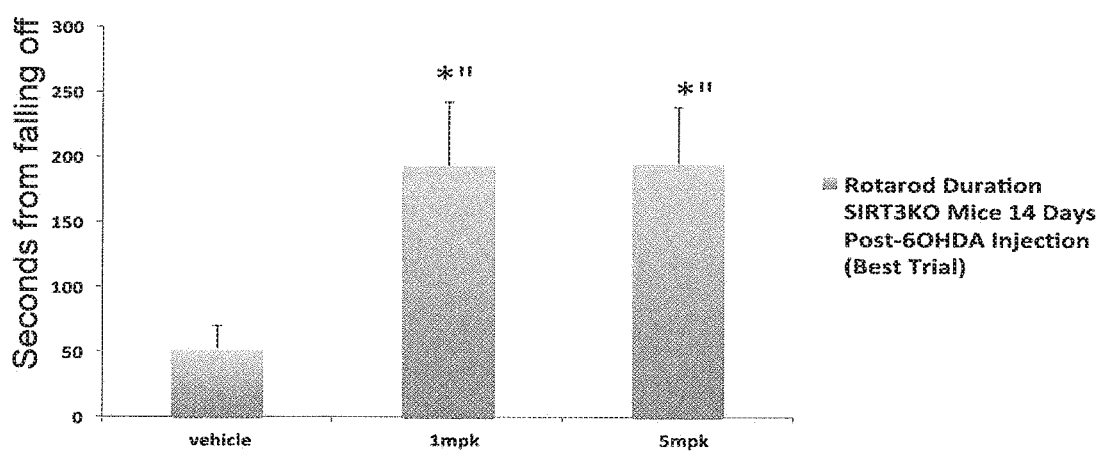
FIG. 7b depicts the results of another mouse study whereby mice were treated with DNP for 14 days to see the impact on protecting dopaminergic neuronal loss.

FIGS. 7a and 7b show the effects of DNP (MP101) treatment for 14-Days by oral gavage in protecting dopaminergic neuronal loss when the right striatum is injected with 6-OHDA after the last day. FIG. 7a show that when the mice are placed in a cylinder, the percent of left and right paw touches on the wall is improved in wildtype mice, and FIG. 7b shows that in the SIRT3 KO mice, which are more vulnerable to Parkinson's disease, there is improved motor coordination when treated with MP101 (DNP) and placed on a rotating cylinder (rotarod).

MP101 (DNP) was used in a mouse model of Huntington's Disease, the "Fragment Model" N171-82 HD mice, to determine its neuroprotective effects. The N171-82 HD mice were treated with MP101 at 0.5, 1 and 5 mg/kg by oral gavage daily for greater than 17-weeks. At the age of 26-weeks (17-weeks of treatment), the mice were tested for changes in behavioral, loss of brain volume, spiny neurons and general neurons. FIGS. 8a, 8b, 8c, 8d, 8e, and 8f show the effects of DNP (MP101 drug treatment).

Figure 8D:
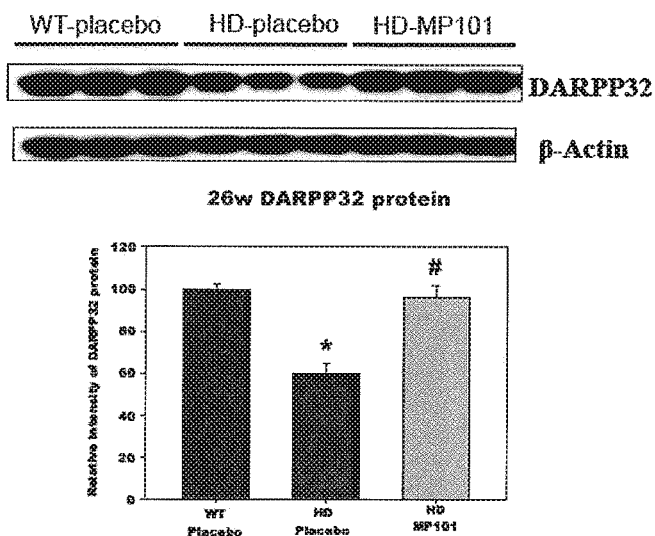
FIG. 8d depicts the results of a mouse study showing that treatment with DNP preserves medium spiny neurons using biomarker DARPP32 at 26-weeks of age.
Figure 8E:
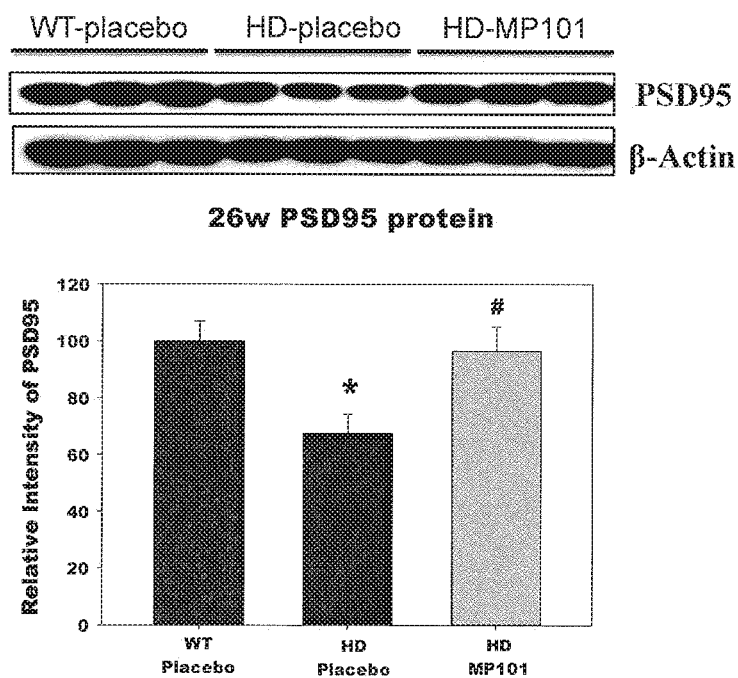
FIG. 8e depicts the results of a mouse study showing that treatment with DNP preserves general neuronal loss with biomarker to postsynaptic protein PSD95 levels in N171-82Q HD mice.
Figure 8F:
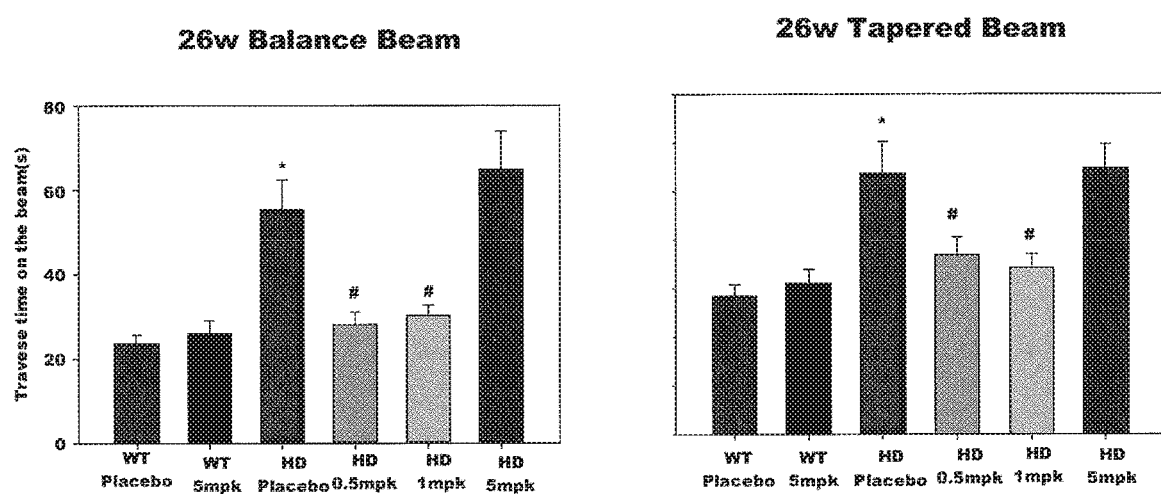
FIG. 8f depicts the results of a mouse study showing that treatment with DNP improves motor function in both the taper beam and balance beam after 17-weeks of treatment.

FIGS. 8a-8f show the effects of MP101 in the Huntington's Disease model N171-82Q after 13-weeks (age 22 weeks) and/or 17-weeks (age 26-weeks) of treatment with DNP. FIG. 8a shows an MM image of brain volume changes of wildtype (WT), mutant Huntington mice Vehicle (HD) and MP101 treated mice (HD-MP101). FIG. 8b shows the quantitative brain volume loss in the cortex. FIG. 8c shows the quantitative brain volume loss in the striatum. HD placebo (HD) shows loss in both Ctx and Str. MP-101 shows minor loss in cortex and striatum. FIG. 8d shows that treatment with DNP preserves medium spiny neurons using biomarker DARPP32 at 26-weeks of age. FIG. 8e shows that treatment with DNP preserves general neuronal loss with biomarker to postsynaptic protein PSD95 levels in N171-82Q HD mice. FIG. 8f shows that treatment with DNP improves motor function in both the tapered beam and balance beam after 17-weeks of treatment.

In view of the foregoing, the present invention describes methods and formulations related to the effective use of DNP to increase BDNF to attenuate disease progression or provide remission of symptoms in certain diseases.

Method of Use

In one embodiment, a method of use of the invention may include a method of treating a neurodegenerative, neuromuscular, developmental, metabolic, auto-immune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.001 mg/kg of body weight to 5 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.001 mg/kg of body weight to about 5 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.01 mg/kg of body weight to 5 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.01 mg/kg of body weight to about 5 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.01 mg/kg of body weight to 1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.01 mg/kg of body weight to about 1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.005 mg/kg of body weight to 2 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.005 mg/kg of body weight to about 2 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.02 mg/kg of body weight to 0.9 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.02 mg/kg of body weight to about 0.9 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.02 mg/kg of body weight to 0.06 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.02 mg/kg of body weight to about 0.06 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.05 mg/kg of body weight to 0.09 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.05 mg/kg of body weight to about 0.09 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.2 mg/kg of body weight to 0.6 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.2 mg/kg of body weight to about 0.6 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.5 mg/kg of body weight to 0.9 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.5 mg/kg of body weight to about 0.9 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.01 mg/kg of body weight to 0.1 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.01 mg/kg of body weight to about 0.1 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.01 mg/kg of body weight to 0.5 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.01 mg/kg of body weight to about 0.5 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.05 mg/kg of body weight to 0.5 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.05 mg/kg of body weight to about 0.5 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.05 mg/kg of body weight to 0.9 mg/kg of body weight to increase BDNF to attenuate disease progression or provide remission of symptoms.

In one embodiment, a method of use of the invention may include a method of treating a neurodegenerative, neuromuscular, developmental, metabolic, autoimmune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.05 mg/kg of body weight to about 0.9 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.02 mg/kg of body weight to 1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging and any of the aforementioned diseases or conditions, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.02 mg/kg of body weight to about 1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.01 mg/kg of body weight to 0.1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.01 mg/kg of body weight to about 0.1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of 0.1 mg/kg of body weight to 1 mg/kg of body weight to increase BDNF to attenuate disease progression or provide remission of symptoms.

In one embodiment, a method of use of the invention may include a method of treating a neurodegenerative, neuromuscular, developmental, metabolic, auto-immune or mitochondrial disorder, including those related to aging, comprising administering to a patient in need of treatment an effective dose of DNP, or a pharmaceutically acceptable salt thereof, over a period sufficiently long to achieve remission of the symptoms of the disease, wherein the effective dose of the DNP is continued in the dose range of about 0.1 mg/kg of body weight to about 1 mg/kg of body weight to increase BDNF to attenuate disease progression or provide remission of symptoms.

In one embodiment, a method of use of the invention may include a method of treating neuromuscular or neurodegenerative disorder related to aging, comprising administering to a patient in need of treatment of a traumatic CNS injury or neurodegenerative disease an effective dose of DNP, or a pharmaceutically acceptable salt thereof, over a period sufficiently long to achieve remission of the symptoms of the disease, wherein the effective dose of the DNP is continued in the dose range of 1 mg/kg of body weight to 5 mg/kg of body weight to increase BDNF to attenuate disease progression or provide remission of symptoms.

In one embodiment, a method of use of the invention may include a method of treating neuromuscular or neurodegenerative disorder related to aging, comprising administering to a patient in need of treatment of a traumatic CNS injury or neurodegenerative disease an effective dose of DNP, or a pharmaceutically acceptable salt thereof, over a period sufficiently long to achieve remission of the symptoms of the disease, wherein the effective dose of the DNP is continued in the dose range of about 1 mg/kg of body weight to about 5 mg/kg of body weight to increase BDNF to attenuate disease progression or provide remission of symptoms.

In an embodiment, administration of DNP, or a pharmaceutically acceptable salt thereof, in any form or combination as described herein, for any purpose as described herein, is in the dose range of about 0.001 mg/kg of body weight to about 5 mg/kg of body weight, about 0.001 mg/kg of body weight to about 4 mg/kg of body weight, about 0.001 mg/kg of body weight to about 3 mg/kg of body weight, about 0.001 mg/kg of body weight to about 0.005 mg/kg of body weight, about 0.005 mg/kg of body weight to about 0.01 mg/kg of body weight, about 0.01 mg/kg of body weight to about 1 of body weight, about 0.01 mg/kg of body weight to about 0.1 of body weight, about 0.02 mg/kg of body weight to about 0.08 of body weight, about 0.025 mg/kg of body weight to about 0.06 of body weight, about 0.03 mg/kg of body weight to about 0.05 of body weight, about 0.05 mg/kg of body weight to about 0.1 of body weight, about 0.04 mg/kg of body weight to about 0.06 of body weight, about 0.06 mg/kg of body weight to about 0.09 of body weight, about 0.07 mg/kg of body weight to about 0.08 of body weight, about 0.09 mg/kg of body weight to about 0.11 of body weight, about 0.1 mg/kg of body weight to about 0.5 of body weight, about 0.2 mg/kg of body weight to about 0.4 of body weight, about 0.3 mg/kg of body weight to about 0.5 of body weight, about 0.4 mg/kg of body weight to about 0.6 of body weight, about 0.5 mg/kg of body weight to about 1 of body weight, about 0.6 mg/kg of body weight to about 0.9 of body weight, about 0.7 mg/kg of body weight to about 0.8 of body weight, about 0.8 mg/kg of body weight to about 1.2 mg/kg of body weight, about 1 mg/kg of body weight to about 5 mg/kg of body weight, or about 2 mg/kg of body weight to about 4 of body weight.

In an embodiment, administration of DNP, or a pharmaceutically acceptable salt thereof, in any form or combination as described herein, for any purpose as described herein, is in the dose range of 0.001 mg/kg of body weight to 5 mg/kg of body weight, 0.001 mg/kg of body weight to 4 mg/kg of body weight, 0.001 mg/kg of body weight to 3 mg/kg of body weight, 0.001 mg/kg of body weight to 0.005 mg/kg of body weight, 0.005 mg/kg of body weight to 0.01 mg/kg of body weight, 0.01 mg/kg of body weight to 1 of body weight, 0.01 mg/kg of body weight to 0.1 of body weight, 0.02 mg/kg of body weight to 0.08 of body weight, 0.025 mg/kg of body weight to 0.06 of body weight, 0.03 mg/kg of body weight to 0.05 of body weight, 0.05 mg/kg of body weight to 0.1 of body weight, 0.04 mg/kg of body weight to 0.06 of body weight, 0.06 mg/kg of body weight to 0.09 of body weight, 0.07 mg/kg of body weight to 0.08 of body weight, 0.09 mg/kg of body weight to 0.11 of body weight, 0.1 mg/kg of body weight to 0.5 of body weight, 0.2 mg/kg of body weight to 0.4 of body weight, 0.3 mg/kg of body weight to 0.5 of body weight, 0.4 mg/kg of body weight to 0.6 of body weight, 0.5 mg/kg of body weight to 1 of body weight, 0.6 mg/kg of body weight to 0.9 of body weight, 0.7 mg/kg of body weight to 0.8 of body weight, 0.8 mg/kg of body weight to 1.2 mg/kg of body weight, 1 mg/kg of body weight to 5 mg/kg of body weight, or 2 mg/kg of body weight to 4 of body weight.

In an embodiment, administration of DNP, or a pharmaceutically acceptable salt thereof, in any form or combination as described herein, for any purpose as described herein, is about 0.001 mg/kg, about 0.002 mg/kg, about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.015 mg/kg, about 0.02 mg/kg, about 0.025 mg/kg, about 0.03 mg/kg, about 0.035 mg/kg, about 0.04 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, about 1.5 mg/kg, about 2 mg/kg, about 2.5 mg/kg, about 3 mg/kg, about 3.5 mg/kg, about 4 mg/kg, about 4.5 mg/kg, or about 5.0 mg/kg.

In an embodiment, administration of DNP, or a pharmaceutically acceptable salt thereof, in any form or combination as described herein, for any purpose as described herein, is 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, about 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 2 mg/kg, 2.5 mg/kg, 3 mg/kg, 3.5 mg/kg, 4 mg/kg, 4.5 mg/kg, or 5.0 mg/kg.

In an embodiment, administration of DNP, or a pharmaceutically acceptable salt thereof, in any form or combination as described herein, for any purpose as described herein, is about 10 mg/kg of body weight or less, about 5 mg/kg of body weight or less, about 4.5 mg/kg or less, about 4 mg/kg or less, about 3.5 mg/kg or less, about 3 mg/kg or less, about 2.5 mg/kg or less, about 2 mg/kg or less, about 1.5 mg/kg or less, about 1 mg/kg or less, about 0.95 mg/kg or less, about 0.9 mg/kg or less, about 0.85 mg/kg or less, about 0.8 mg/kg or less, about 0.75 mg/kg or less, about 0.7 mg/kg or less, about 0.65 mg/kg or less, about 0.6 mg/kg or less, about 0.55 mg/kg or less, about 0.5 mg/kg or less, about 0.45 mg/kg or less, about 0.4 mg/kg or less, about 0.35 mg/kg or less, about 0.3 mg/kg or less, about 0.25 mg/kg or less, about 0.2 mg/kg or less, about 0.15 mg/kg or less, about 0.1 mg/kg or less, about 0.09 mg/kg or less, about 0.08 mg/kg or less, about 0.07 mg/kg or less, about 0.06 mg/kg or less, about 0.05 mg/kg or less, about 0.04 mg/kg or less, about 0.03 mg/kg or less, about 0.02 mg/kg or less, about 0.01 mg/kg or less, or about 0.005 mg/kg or less. In all cases, the doses described herein are greater than zero mg/kg.

In an embodiment, administration of DNP, or a pharmaceutically acceptable salt thereof, in any form or combination as described herein, for any purpose as described herein, is about 4 mg/kg or more, about 3.5 mg/kg or more, about 3 mg/kg or more, about 2.5 mg/kg or more, about 2 mg/kg or more, about 1.5 mg/kg or more, about 1 mg/kg or more, about 0.95 mg/kg or more, about 0.9 mg/kg or more, about 0.85 mg/kg or more, about 0.8 mg/kg or more, about 0.75 mg/kg or more, about 0.7 mg/kg or more, about 0.65 mg/kg or more, about 0.6 mg/kg or more, about 0.55 mg/kg or more, about 0.5 mg/kg or more, about 0.45 mg/kg or more, about 0.4 mg/kg or more, about 0.35 mg/kg or more, about 0.3 mg/kg or more, about 0.25 mg/kg or more, about 0.2 mg/kg or more, about 0.15 mg/kg or more, about 0.1 mg/kg or more, about 0.09 mg/kg or more, about 0.08 mg/kg or more, about 0.07 mg/kg or more, about 0.06 mg/kg or more, about 0.05 mg/kg or more, about 0.04 mg/kg or more, about 0.03 mg/kg or more, about 0.02 mg/kg or more, about 0.01 mg/kg or more, about 0.009 mg/kg or more, about 0.007 mg/kg or more, about 0.005 mg/kg or more, about 0.003 mg/kg or more, or about 0.001 mg/kg or more. In all cases, the doses described herein are less than 10 mg/kg.

In some examples, the effective dose is delivered orally. In some examples, the effective does is delivered intravenously. In some examples, the effective does is delivered intravenously by means of an intravenous drip along with saline. In some examples, the effective does is delivered intravenously by means of an intravenous drip along with other medicines, vitamins, fluids or nutrition. In some examples, the effective does is delivered subcutaneously. In some examples, the effective dose is delivered topically. In some examples, the effective dose is delivered transdermally. In some examples, the effective dose is combined with other necessary medicines, vitamins, fluids or nutrition.

In some examples, the effective dose is used to treat, prevent or alleviate any of the following diseases or conditions by inducing BDNF with DNP treatment: Traumatic Brain Injury (TBI), Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity Onset Diabetes of the Young (MODY: MODY1, MODY2, MODY3, MODY4, MODY5, MODY6, MODY7, MODY8, MODY9, MODY10, MODY11)), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD), Becker, Myotonic, Congenital, Emery-Dreifuss, Facioscapulohumeral, Limb-girdle, Distal, and Oculopharyngeal), severe burns, aging, Amyotrophic Lateral Sclerosis (ALS), Ataxia (Friedreich's Ataxia, Spinocerebellar ataxias 1 (SCA1), Spinocerebellar ataxias 2 (SCA2), Spinocerebellar ataxias 3 (SCA3), Spinocerebellar ataxias 6 (SCA6), Spinocerebellar ataxias 7 (SCA7), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), mitochondrial diseases, developmental disorders, metabolic syndrome (increased blood pressure, high blood sugar level, excess body fat around the waist and abnormal cholesterol levels) and/or autoimmune disorders.

In some examples, the effective dose used to treat, prevent or alleviate the symptoms of Huntington's disease is 0.005 mg/kg to 1.0 mg/kg. In some examples, the effective dose used to treat, prevent or alleviate Huntington's disease is 0.01 mg/kg to 0.5 mg/kg. In some examples, the effective dose used to treat, prevent or alleviate Huntington's disease is 0.01 mg/kg to 0.1 mg/kg. In some examples, the effective dose used to treat, prevent or alleviate Huntington's disease is 0.02 mg/kg to 0.1 mg/kg. In some examples, the effective dose used to treat, prevent or alleviate Huntington's disease is 0.02 mg/kg to 0.4 mg/kg. In some examples, the effective dose used to treat, prevent or alleviate Huntington's disease is 0.025 mg/kg to 0.4 mg/kg. In some examples, the effective dose used to treat, prevent or alleviate Huntington's disease is 0.025 mg/kg to 0.08 mg/kg. In some examples, the effective dose used to treat, prevent or alleviate Huntington's disease is 0.03 mg/kg to 0.075 mg/kg. In some examples, the effective dose used to treat, prevent or alleviate Huntington's disease is 0.035 mg/kg to 0.4 mg/kg. In some examples, the effective dose used to treat, prevent or alleviate Huntington's disease is 0.035 mg/kg to 0.1 mg/kg. In some examples, the effective dose used to treat, prevent or alleviate Huntington's disease is 0.035 mg/kg to 0.09 mg/kg. In some examples, the effective dose used to treat, prevent or alleviate Huntington's disease is 0.035 mg/kg to 0.08 mg/kg. In some examples, the effective dose used to treat, prevent or alleviate Huntington's disease is 0.035 mg/kg to 0.075 mg/kg. In some examples, the effective dose used to treat, prevent or alleviate Huntington's disease is 0.045 mg/kg to 0.055 mg/kg. In some examples, the effective dose used to treat, prevent or alleviate Huntington's disease is 0.055 mg/kg to 0.085 mg/kg. In some examples, the effective dose used to treat, prevent or alleviate Huntington's disease is 0.055 mg/kg to 0.065 mg/kg. In some examples, the effective dose used to treat, prevent or alleviate Huntington's disease is 0.065 mg/kg to 0.075 mg/kg. In some examples, the effective dose used to treat, prevent or alleviate Huntington's disease is 0.075 mg/kg to 0.1 mg/kg. In some examples, the effective dose used to treat, prevent or alleviate Huntington's disease is 0.07 mg/kg to 0.09 mg/kg. In some examples, the effective dose used to treat, prevent or alleviate Huntington's disease is 0.085 mg/kg to 0.1 mg/kg. In some examples, the effective dose used to treat, prevent or alleviate Huntington's disease is 0.09 mg/kg to 0.2 mg/kg. In some examples, the effective dose used to treat, prevent or alleviate Huntington's disease is 0.1 mg/kg to 0.3 mg/kg. In some examples, the effective dose used to treat, prevent or alleviate Huntington's disease is 0.2 mg/kg to 0.4 mg/kg.

In some examples, the effective dose used to treat, prevent or alleviate the symptoms of Huntington's disease is about 0.005 mg/kg to about 1.0 mg/kg. In some examples, the effective dose used to treat, prevent or alleviate Huntington's disease is about 0.01 mg/kg to about 0.5 mg/kg. In some examples, the effective dose used to treat, prevent or alleviate Huntington's disease is about 0.01 mg/kg to about 0.1 mg/kg. In some examples, the effective dose used to treat, prevent or alleviate Huntington's disease is about 0.02 mg/kg to about 0.1 mg/kg. In some examples, the effective dose used to treat, prevent or alleviate Huntington's disease is about 0.02 mg/kg to about 0.4 mg/kg. In some examples, the effective dose used to treat, prevent or alleviate Huntington's disease is about 0.025 mg/kg to about 0.4 mg/kg. In some examples, the effective dose used to treat, prevent or alleviate Huntington's disease is about 0.025 mg/kg to about 0.08 mg/kg. In some examples, the effective dose used to treat, prevent or alleviate Huntington's disease is about 0.03 mg/kg to about 0.075 mg/kg. In some examples, the effective dose used to treat, prevent or alleviate Huntington's disease is about 0.035 mg/kg to about 0.4 mg/kg. In some examples, the effective dose used to treat, prevent or alleviate Huntington's disease is about 0.035 mg/kg to about 0.1 mg/kg. In some examples, the effective dose used to treat, prevent or alleviate Huntington's disease is about 0.035 mg/kg to about 0.09 mg/kg. In some examples, the effective dose used to treat, prevent or alleviate Huntington's disease is about 0.035 mg/kg to about 0.08 mg/kg. In some examples, the effective dose used to treat, prevent or alleviate Huntington's disease is about 0.035 mg/kg to about 0.075 mg/kg. In some examples, the effective dose used to treat, prevent or alleviate Huntington's disease is about 0.045 mg/kg to about 0.055 mg/kg. In some examples, the effective dose used to treat, prevent or alleviate Huntington's disease is about 0.055 mg/kg to about 0.085 mg/kg. In some examples, the effective dose used to treat, prevent or alleviate Huntington's disease is about 0.055 mg/kg to about 0.065 mg/kg. In some examples, the effective dose used to treat, prevent or alleviate Huntington's disease is about 0.065 mg/kg to about 0.075 mg/kg. In some examples, the effective dose used to treat, prevent or alleviate Huntington's disease is about 0.075 mg/kg to about 0.1 mg/kg. In some examples, the effective dose used to treat, prevent or alleviate Huntington's disease is about 0.07 mg/kg to about 0.09 mg/kg. In some examples, the effective dose used to treat, prevent or alleviate Huntington's disease is about 0.085 mg/kg to about 0.1 mg/kg. In some examples, the effective dose used to treat, prevent or alleviate Huntington's disease is about 0.09 mg/kg to about 0.2 mg/kg. In some examples, the effective dose used to treat, prevent or alleviate Huntington's disease is about 0.1 mg/kg to about 0.3 mg/kg. In some examples, the effective dose used to treat, prevent or alleviate Huntington's disease is about 0.2 mg/kg to about 0.4 mg/kg.

In some examples, the effective dose used to treat, prevent or alleviate the symptoms of Huntington's disease is 0.001 mg/kg or more. In some examples, the effective dose used to treat, prevent or alleviate the symptoms of Huntington's disease is 0.002 mg/kg or more. In some examples, the effective dose used to treat, prevent or alleviate the symptoms of Huntington's disease is 0.003 mg/kg or more. In some examples, the effective dose used to treat, prevent or alleviate the symptoms of Huntington's disease is 0.004 mg/kg or more. In some examples, the effective dose used to treat, prevent or alleviate the symptoms of Huntington's disease is 0.005 mg/kg or more. In some examples, the effective dose used to treat, prevent or alleviate the symptoms of Huntington's disease is 0.01 mg/kg or more. In some examples, the effective dose used to treat, prevent or alleviate the symptoms of Huntington's disease is 0.025 mg/kg or more. In some examples, the effective dose used to treat, prevent or alleviate the symptoms of Huntington's disease is 0.035 mg/kg or more. In some examples, the effective dose used to treat, prevent or alleviate the symptoms of Huntington's disease is 0.05 mg/kg or more. In some examples, the effective dose used to treat, prevent or alleviate the symptoms of Huntington's disease is 0.075 mg/kg or more. In some examples, the effective dose used to treat, prevent or alleviate the symptoms of Huntington's disease is 0.1 mg/kg or more. In some examples, the effective dose used to treat, prevent or alleviate the symptoms of Huntington's disease is 1 mg/kg or less. In some examples, the effective dose used to treat, prevent or alleviate the symptoms of Huntington's disease is 0.5 mg/kg or less. In some examples, the effective dose used to treat, prevent or alleviate the symptoms of Huntington's disease is 0.35 mg/kg or less. In some examples, the effective dose used to treat, prevent or alleviate the symptoms of Huntington's disease is 0.25 mg/kg or less. In some examples, the effective dose used to treat, prevent or alleviate the symptoms of Huntington's disease is 0.1 mg/kg or less. In some examples, the effective dose used to treat, prevent or alleviate the symptoms of Huntington's disease is 0.075 mg/kg or less. In some examples, the effective dose used to treat, prevent or alleviate the symptoms of Huntington's disease is 0.05 mg/kg or less. In some examples, the effective dose used to treat, prevent or alleviate the symptoms of Huntington's disease is 0.01 mg/kg or less. In all cases, the dose described herein is greater than zero mg/kg and less than 5 mg/kg.

In some examples, the effective dose used to treat, prevent or alleviate the symptoms of Multiple Sclerosis (MS) is 0.01 mg/kg to 5 mg/kg. In some examples, the effective dose used to treat, prevent or alleviate the symptoms of Multiple Sclerosis (MS) is 0.01 mg/kg to 1 mg/kg. In some examples, the effective dose used to treat, prevent or alleviate the symptoms of Multiple Sclerosis (MS) is 0.05 mg/kg to 5 mg/kg. In some examples, the effective dose used to treat, prevent or alleviate the symptoms of Multiple Sclerosis (MS) is 0.05 mg/kg to 1 mg/kg. In some examples, the effective dose used to treat, prevent or alleviate Multiple Sclerosis (MS) is 0.06 mg/kg to 1 mg/kg. In some examples, the effective dose used to treat, prevent or alleviate Multiple Sclerosis (MS) is 0.07 mg/kg to 0.9 mg/kg. In some examples, the effective dose used to treat, prevent or alleviate Multiple Sclerosis (MS) is 0.075 mg/kg to 0.8 mg/kg. In some examples, the effective dose used to treat, prevent or alleviate Multiple Sclerosis (MS) is 0.07 mg/kg to 0.1 mg/kg. In some examples, the effective dose used to treat, prevent or alleviate Multiple Sclerosis (MS) is 0.08 mg/kg to 0.5 mg/kg. In some examples, the effective dose used to treat, prevent or alleviate Multiple Sclerosis (MS) is 0.1 mg/kg to 0.8 mg/kg. In some examples, the effective dose used to treat, prevent or alleviate Multiple Sclerosis (MS) is 0.3 mg/kg to 0.8 mg/kg. In some examples, the effective dose used to treat, prevent or alleviate Multiple Sclerosis (MS) is 0.4 mg/kg to 0.7 mg/kg. In some examples, the effective dose used to treat, prevent or alleviate Multiple Sclerosis (MS) is 0.7 mg/kg to 0.8 mg/kg. In some examples, the effective dose used to treat, prevent or alleviate Multiple Sclerosis (MS) is 0.8 mg/kg to 1 mg/kg.

In some examples, the effective dose used to treat, prevent or alleviate the symptoms of Multiple Sclerosis (MS) is about 0.05 mg/kg to about 5 mg/kg. In some examples, the effective dose used to treat, prevent or alleviate the symptoms of Multiple Sclerosis (MS) is about 0.01 mg/kg to about 1 mg/kg. In some examples, the effective dose used to treat, prevent or alleviate the symptoms of Multiple Sclerosis (MS) is about 0.05 mg/kg to about 5 mg/kg. In some examples, the effective dose used to treat, prevent or alleviate the symptoms of Multiple Sclerosis (MS) is about 0.05 mg/kg to about 1 mg/kg. In some examples, the effective dose used to treat, prevent or alleviate Multiple Sclerosis (MS) is about 0.06 mg/kg to about 1 mg/kg. In some examples, the effective dose used to treat, prevent or alleviate Multiple Sclerosis (MS) is about 0.07 mg/kg to about 0.9 mg/kg. In some examples, the effective dose used to treat, prevent or alleviate Multiple Sclerosis (MS) is about 0.075 mg/kg to about 0.8 mg/kg. In some examples, the effective dose used to treat, prevent or alleviate Multiple Sclerosis (MS) is about 0.07 mg/kg to about 0.1 mg/kg. In some examples, the effective dose used to treat, prevent or alleviate Multiple Sclerosis (MS) is about 0.08 mg/kg to about 0.5 mg/kg. In some examples, the effective dose used to treat, prevent or alleviate Multiple Sclerosis (MS) is about 0.1 mg/kg to about 0.8 mg/kg. In some examples, the effective dose used to treat, prevent or alleviate Multiple Sclerosis (MS) is about 0.3 mg/kg to about 0.8 mg/kg. In some examples, the effective dose used to treat, prevent or alleviate Multiple Sclerosis (MS) is about 0.4 mg/kg to about 0.7 mg/kg. In some examples, the effective dose used to treat, prevent or alleviate Multiple Sclerosis (MS) is about 0.7 mg/kg to about 0.8 mg/kg. In some examples, the effective dose used to treat, prevent or alleviate Multiple Sclerosis (MS) is about 0.8 mg/kg to about 1 mg/kg.

In some examples, the effective dose used to treat, prevent or alleviate Multiple Sclerosis (MS) is 1.0 mg/kg or less. In some examples, the effective dose used to treat, prevent or alleviate Multiple Sclerosis (MS) is 0.9 mg/kg or less. In some examples, the effective dose used to treat, prevent or alleviate Multiple Sclerosis (MS) is 0.8 mg/kg or less. In some examples, the effective dose used to treat, prevent or alleviate Multiple Sclerosis (MS) is 0.7 mg/kg or less. In some examples, the effective dose used to treat, prevent or alleviate Multiple Sclerosis (MS) is 0.6 mg/kg or less. In some examples, the effective dose used to treat, prevent or alleviate Multiple Sclerosis (MS) is 0.5 mg/kg or less. In some examples, the effective dose used to treat, prevent or alleviate Multiple Sclerosis (MS) is 0.4 mg/kg or less. In some examples, the effective dose used to treat, prevent or alleviate Multiple Sclerosis (MS) is 0.3 mg/kg or less. In some examples, the effective dose used to treat, prevent or alleviate Multiple Sclerosis (MS) is 0.2 mg/kg or less. In some examples, the effective dose used to treat, prevent or alleviate Multiple Sclerosis (MS) is 0.1 mg/kg or less. In some examples, the effective dose used to treat, prevent or alleviate Multiple Sclerosis (MS) is 0.09 mg/kg or less. In some examples, the effective dose used to treat, prevent or alleviate Multiple Sclerosis (MS) is 0.08 mg/kg or less. In some examples, the effective dose used to treat, prevent or alleviate Multiple Sclerosis (MS) is 0.07 mg/kg or less. In some examples, the effective dose used to treat, prevent or alleviate Multiple Sclerosis (MS) is 0.05 mg/kg or less. In some examples, the effective dose used to treat, prevent or alleviate Multiple Sclerosis (MS) is 0.01 mg/kg or more. In some examples, the effective dose used to treat, prevent or alleviate Multiple Sclerosis (MS) is 0.05 mg/kg or more. In some examples, the effective dose used to treat, prevent or alleviate Multiple Sclerosis (MS) is 0.06 mg/kg or more. In some examples, the effective dose used to treat, prevent or alleviate Multiple Sclerosis (MS) is 0.07 mg/kg or more. In some examples, the effective dose used to treat, prevent or alleviate Multiple Sclerosis (MS) is 0.08 mg/kg or more. In some examples, the effective dose used to treat, prevent or alleviate Multiple Sclerosis (MS) is 0.09 mg/kg or more. In some examples, the effective dose used to treat, prevent or alleviate Multiple Sclerosis (MS) is 0.1 mg/kg or more. In some examples, the effective dose used to treat, prevent or alleviate Multiple Sclerosis (MS) is 0.15 mg/kg or more. In some examples, the effective dose used to treat, prevent or alleviate Multiple Sclerosis (MS) is 0.2 mg/kg or more. In some examples, the effective dose used to treat, prevent or alleviate Multiple Sclerosis (MS) is 0.25 mg/kg or more. In some examples, the effective dose used to treat, prevent or alleviate Multiple Sclerosis (MS) is 0.3 mg/kg or more. In some examples, the effective dose used to treat, prevent or alleviate Multiple Sclerosis (MS) is 0.35 mg/kg or more. In some examples, the effective dose used to treat, prevent or alleviate Multiple Sclerosis (MS) is 0.4 mg/kg or more. In some examples, the effective dose used to treat, prevent or alleviate Multiple Sclerosis (MS) is 0.45 mg/kg or more. In some examples, the effective dose used to treat, prevent or alleviate Multiple Sclerosis (MS) is 0.5 mg/kg or more. In some examples, the effective dose used to treat, prevent or alleviate Multiple Sclerosis (MS) is 0.55 mg/kg or more. In some examples, the effective dose used to treat, prevent or alleviate Multiple Sclerosis (MS) is 0.6 mg/kg or more. In some examples, the effective dose used to treat, prevent or alleviate Multiple Sclerosis (MS) is 0.65 mg/kg or more. In some examples, the effective dose used to treat, prevent or alleviate Multiple Sclerosis (MS) is 0.70 mg/kg or more. In some examples, the effective dose used to treat, prevent or alleviate Multiple Sclerosis (MS) is 0.75 mg/kg or more. In some examples, the effective dose used to treat, prevent or alleviate Multiple Sclerosis (MS) is 0.8 mg/kg or more. In some examples, the effective dose used to treat, prevent or alleviate Multiple Sclerosis (MS) is 1.0 mg/kg or more. In all cases, the dose described herein is greater than zero mg/kg and less than 5 mg/kg.

In some examples, the effective dose used to treat, prevent or alleviate Epilepsy is 0.05 mg/kg to 1 mg/kg. In some examples, the effective dose used to treat, prevent or alleviate Epilepsy is 0.5 mg/kg to 1 mg/kg. In some examples, the effective dose used to treat, prevent or alleviate Epilepsy is 0.6 mg/kg to 0.9 mg/kg. In some examples, the effective dose used to treat, prevent or alleviate Epilepsy is 0.7 mg/kg to 0.8 mg/kg. In some examples, the effective dose used to treat, prevent or alleviate Epilepsy is about 0.5 mg/kg to about 1 mg/kg. In some examples, the effective dose used to treat, prevent or alleviate Epilepsy is about 0.6 mg/kg to about 0.9 mg/kg. In some examples, the effective dose used to treat, prevent or alleviate Epilepsy is about 0.7 mg/kg to about 0.8 mg/kg. In some examples, the effective dose used to treat, prevent or alleviate Epilepsy is 0.1 mg/kg or more. In some examples, the effective dose used to treat, prevent or alleviate Epilepsy is 0.4 mg/kg or more. In some examples, the effective dose used to treat, prevent or alleviate Epilepsy is 0.5 mg/kg or more. In some examples, the effective dose used to treat, prevent or alleviate Epilepsy is 0.6 mg/kg or more. In some examples, the effective dose used to treat, prevent or alleviate Epilepsy is 0.7 mg/kg or more. In some examples, the effective dose used to treat, prevent or alleviate Epilepsy is 0.8 mg/kg or more. In some examples, the effective dose used to treat, prevent or alleviate Epilepsy is 1 mg/kg or less. In some examples, the effective dose used to treat, prevent or alleviate Epilepsy is 0.9 mg/kg or less. In some examples, the effective dose used to treat, prevent or alleviate Epilepsy is 0.8 mg/kg or less. In some examples, the effective dose used to treat, prevent or alleviate Epilepsy is 0.7 mg/kg or less. In some examples, the effective dose used to treat, prevent or alleviate Epilepsy is 0.5 mg/kg or less. In all cases, the dose described herein is greater than zero mg/kg and less than 5 mg/kg.

In some examples, the effective dose used to treat, prevent or alleviate the symptoms of Rett Syndrome is 0.005 mg/kg to 1 mg/kg. In some examples, the effective dose used to treat, prevent or alleviate Rett Syndrome is 0.02 mg/kg to 1 mg/kg. In some examples, the effective dose used to treat, prevent or alleviate Rett Syndrome is 0.01 mg/kg to 0.5 mg/kg. In some examples, the effective dose used to treat, prevent or alleviate Rett Syndrome is 0.02 mg/kg to 0.4 mg/kg. In some examples, the effective dose used to treat, prevent or alleviate Rett Syndrome is 0.025 mg/kg to 0.4 mg/kg. In some examples, the effective dose used to treat, prevent or alleviate Rett Syndrome is 0.025 mg/kg to 0.08 mg/kg. In some examples, the effective dose used to treat, prevent or alleviate Rett Syndrome is 0.03 mg/kg to 0.075 mg/kg. In some examples, the effective dose used to treat, prevent or alleviate Rett Syndrome is 0.035 mg/kg to 0.4 mg/kg. In some examples, the effective dose used to treat, prevent or alleviate Rett Syndrome is 0.035 mg/kg to 0.1 mg/kg. In some examples, the effective dose used to treat, prevent or alleviate Rett Syndrome is 0.035 mg/kg to 0.09 mg/kg. In some examples, the effective dose used to treat, prevent or alleviate Rett Syndrome is 0.035 mg/kg to 0.08 mg/kg. In some examples, the effective dose used to treat, prevent or alleviate Rett Syndrome is 0.035 mg/kg to 0.075 mg/kg. In some examples, the effective dose used to treat, prevent or alleviate Rett Syndrome is 0.045 mg/kg to 0.055 mg/kg. In some examples, the effective dose used to treat, prevent or alleviate Rett Syndrome is 0.055 mg/kg to 0.085 mg/kg. In some examples, the effective dose used to treat, prevent or alleviate Rett Syndrome is 0.055 mg/kg to 0.065 mg/kg. In some examples, the effective dose used to treat, prevent or alleviate Rett Syndrome is 0.065 mg/kg to 0.075 mg/kg. In some examples, the effective dose used to treat, prevent or alleviate Rett Syndrome is 0.075 mg/kg to 0.1 mg/kg. In some examples, the effective dose used to treat, prevent or alleviate Rett Syndrome is 0.07 mg/kg to 0.09 mg/kg. In some examples, the effective dose used to treat, prevent or alleviate Rett Syndrome is 0.085 mg/kg to 0.1 mg/kg. In some examples, the effective dose used to treat, prevent or alleviate Rett Syndrome is 0.09 mg/kg to 0.2 mg/kg.

In some examples, the effective dose used to treat, prevent or alleviate the symptoms of Rett Syndrome is about 0.005 mg/kg to about 1.0 mg/kg. In some examples, the effective dose used to treat, prevent or alleviate Rett Syndrome is about 0.02 mg/kg to about 1 mg/kg. In some examples, the effective dose used to treat, prevent or alleviate Rett Syndrome is about 0.01 mg/kg to about 0.5 mg/kg. In some examples, the effective dose used to treat, prevent or alleviate Rett Syndrome is about 0.02 mg/kg to about 0.4 mg/kg. In some examples, the effective dose used to treat, prevent or alleviate Rett Syndrome is about 0.025 mg/kg to about 0.4 mg/kg. In some examples, the effective dose used to treat, prevent or alleviate Rett Syndrome is about 0.025 mg/kg to about 0.08 mg/kg. In some examples, the effective dose used to treat, prevent or alleviate Rett Syndrome is about 0.03 mg/kg to about 0.075 mg/kg. In some examples, the effective dose used to treat, prevent or alleviate Rett Syndrome is about 0.035 mg/kg to about 0.4 mg/kg. In some examples, the effective dose used to treat, prevent or alleviate Rett Syndrome is about 0.035 mg/kg to about 0.1 mg/kg. In some examples, the effective dose used to treat, prevent or alleviate Rett Syndrome is about 0.035 mg/kg to about 0.09 mg/kg. In some examples, the effective dose used to treat, prevent or alleviate Rett Syndrome is about 0.035 mg/kg to about 0.08 mg/kg. In some examples, the effective dose used to treat, prevent or alleviate Rett Syndrome is about 0.035 mg/kg to about 0.075 mg/kg. In some examples, the effective dose used to treat, prevent or alleviate Rett Syndrome is about 0.045 mg/kg to about 0.055 mg/kg. In some examples, the effective dose used to treat, prevent or alleviate Rett Syndrome is about 0.055 mg/kg to about 0.085 mg/kg. In some examples, the effective dose used to treat, prevent or alleviate Rett Syndrome is about 0.055 mg/kg to about 0.065 mg/kg. In some examples, the effective dose used to treat, prevent or alleviate Rett Syndrome is about 0.065 mg/kg to about 0.075 mg/kg. In some examples, the effective dose used to treat, prevent or alleviate Rett Syndrome is about 0.075 mg/kg to about 0.1 mg/kg. In some examples, the effective dose used to treat, prevent or alleviate Rett Syndrome is about 0.07 mg/kg to about 0.09 mg/kg. In some examples, the effective dose used to treat, prevent or alleviate Rett Syndrome is about 0.085 mg/kg to about 0.1 mg/kg. In some examples, the effective dose used to treat, prevent or alleviate Rett Syndrome is about 0.09 mg/kg to about 0.2 mg/kg.

In some examples, the effective dose used to treat, prevent or alleviate the symptoms of Rett Syndrome is 0.01 mg/kg or more. In some examples, the effective dose used to treat, prevent or alleviate the symptoms of Rett Syndrome is 0.02 mg/kg or more. In some examples, the effective dose used to treat, prevent or alleviate the symptoms of Rett Syndrome is 0.03 mg/kg or more. In some examples, the effective dose used to treat, prevent or alleviate the symptoms of Rett Syndrome is 0.04 mg/kg or more. In some examples, the effective dose used to treat, prevent or alleviate the symptoms of Rett Syndrome is 0.05 mg/kg or more. In some examples, the effective dose used to treat, prevent or alleviate the symptoms of Rett Syndrome is 0.06 mg/kg or more. In some examples, the effective dose used to treat, prevent or alleviate the symptoms of Rett Syndrome is 0.07 mg/kg or more. In some examples, the effective dose used to treat, prevent or alleviate the symptoms of Rett Syndrome is 0.08 mg/kg or more. In some examples, the effective dose used to treat, prevent or alleviate the symptoms of Rett Syndrome is 0.09 mg/kg or more. In some examples, the effective dose used to treat, prevent or alleviate the symptoms of Rett Syndrome is 0.5 mg/kg or less. In some examples, the effective dose used to treat, prevent or alleviate the symptoms of Rett Syndrome is 0.3 mg/kg or less. In some examples, the effective dose used to treat, prevent or alleviate the symptoms of Rett Syndrome is 0.1 mg/kg or less. In some examples, the effective dose used to treat, prevent or alleviate the symptoms of Rett Syndrome is 0.075 mg/kg or less. In some examples, the effective dose used to treat, prevent or alleviate the symptoms of Rett Syndrome is 0.05 mg/kg or less. In some examples, the effective dose used to treat, prevent or alleviate the symptoms of Rett Syndrome is 0.01 mg/kg or less. In all cases, the dose described herein is greater than zero mg/kg and less than 5 mg/kg.

In some examples, the effective dose used to treat, prevent or alleviate the symptoms of Parkinson's Disease is 0.01 mg/kg to 1 mg/kg. In some examples, the effective dose used to treat, prevent or alleviate the symptoms of Parkinson's Disease is 0.01 mg/kg to 0.5 mg/kg. In some examples, the effective dose used to treat, prevent or alleviate the symptoms of Parkinson's Disease is 0.05 mg/kg to 0.5 mg/kg. In some examples, the effective dose used to treat, prevent or alleviate Parkinson's Disease is 0.05 mg/kg to 0.1 mg/kg. In some examples, the effective dose used to treat, prevent or alleviate Parkinson's Disease is 0.06 mg/kg to 0.5 mg/kg. In some examples, the effective dose used to treat, prevent or alleviate Parkinson's Disease is 0.07 mg/kg to 0.4 mg/kg. In some examples, the effective dose used to treat, prevent or alleviate Parkinson's Disease is 0.08 mg/kg to 0.4 mg/kg. In some examples, the effective dose used to treat, prevent or alleviate Parkinson's Disease is 0.09 mg/kg to 0.4 mg/kg. In some examples, the effective dose used to treat, prevent or alleviate Parkinson's Disease is 0.075 mg/kg to 0.1 mg/kg. In some examples, the effective dose used to treat, prevent or alleviate Parkinson's Disease is 0.09 mg/kg to 0.2 mg/kg. In some examples, the effective dose used to treat, prevent or alleviate Parkinson's Disease is 0.1 mg/kg to 0.4 mg/kg. In some examples, the effective dose used to treat, prevent or alleviate Parkinson's Disease is 0.2 mg/kg to 0.5 mg/kg.

In some examples, the effective dose used to treat, prevent or alleviate the symptoms of Parkinson's Disease is about 0.01 mg/kg to about 1 mg/kg. In some examples, the effective dose used to treat, prevent or alleviate the symptoms of Parkinson's Disease is about 0.01 mg/kg to about 0.5 mg/kg. In some examples, the effective dose used to treat, prevent or alleviate the symptoms of Parkinson's Disease is about 0.05 mg/kg to about 0.5 mg/kg. In some examples, the effective dose used to treat, prevent or alleviate Parkinson's Disease is about 0.05 mg/kg to about 0.1 mg/kg. In some examples, the effective dose used to treat, prevent or alleviate Parkinson's Disease is about 0.06 mg/kg to about 0.5 mg/kg. In some examples, the effective dose used to treat, prevent or alleviate Parkinson's Disease is about 0.07 mg/kg to about 0.4 mg/kg. In some examples, the effective dose used to treat, prevent or alleviate Parkinson's Disease is about 0.08 mg/kg to about 0.4 mg/kg. In some examples, the effective dose used to treat, prevent or alleviate Parkinson's Disease is about 0.09 mg/kg to about 0.4 mg/kg. In some examples, the effective dose used to treat, prevent or alleviate Parkinson's Disease is about 0.075 mg/kg to about 0.1 mg/kg. In some examples, the effective dose used to treat, prevent or alleviate Parkinson's Disease is about 0.09 mg/kg to about 0.2 mg/kg. In some examples, the effective dose used to treat, prevent or alleviate Parkinson's Disease is about 0.1 mg/kg to about 0.4 mg/kg. In some examples, the effective dose used to treat, prevent or alleviate Parkinson's Disease is about 0.2 mg/kg to about 0.5 mg/kg.

In some examples, the effective dose used to treat, prevent or alleviate Parkinson's Disease is 1.0 mg/kg or less. In some examples, the effective dose used to treat, prevent or alleviate Parkinson's Disease is 0.5 mg/kg or less. In some examples, the effective dose used to treat, prevent or alleviate Parkinson's Disease is 0.4 mg/kg or less. In some examples, the effective dose used to treat, prevent or alleviate Parkinson's Disease is 0.3 mg/kg or less. In some examples, the effective dose used to treat, prevent or alleviate Parkinson's Disease is 0.2 mg/kg or less. In some examples, the effective dose used to treat, prevent or alleviate Parkinson's Disease is 0.1 mg/kg or less. In some examples, the effective dose used to treat, prevent or alleviate Parkinson's Disease is 0.09 mg/kg or less. In some examples, the effective dose used to treat, prevent or alleviate Parkinson's Disease is 0.08 mg/kg or less. In some examples, the effective dose used to treat, prevent or alleviate Parkinson's Disease is 0.07 mg/kg or less. In some examples, the effective dose used to treat, prevent or alleviate Parkinson's Disease is 0.05 mg/kg or less. In some examples, the effective dose used to treat, prevent or alleviate Parkinson's Disease is 0.01 mg/kg or more. In some examples, the effective dose used to treat, prevent or alleviate Parkinson's Disease is 0.05 mg/kg or more. In some examples, the effective dose used to treat, prevent or alleviate Parkinson's Disease is 0.06 mg/kg or more. In some examples, the effective dose used to treat, prevent or alleviate Parkinson's Disease is 0.07 mg/kg or more. In some examples, the effective dose used to treat, prevent or alleviate Parkinson's Disease is 0.08 mg/kg or more. In some examples, the effective dose used to treat, prevent or alleviate Parkinson's Disease is 0.09 mg/kg or more. In some examples, the effective dose used to treat, prevent or alleviate Parkinson's Disease is 0.1 mg/kg or more. In some examples, the effective dose used to treat, prevent or alleviate Parkinson's Disease is 0.15 mg/kg or more. In some examples, the effective dose used to treat, prevent or alleviate Parkinson's Disease is 0.2 mg/kg or more. In some examples, the effective dose used to treat, prevent or alleviate Parkinson's Disease is 0.25 mg/kg or more. In some examples, the effective dose used to treat, prevent or alleviate Parkinson's Disease is 0.3 mg/kg or more. In some examples, the effective dose used to treat, prevent or alleviate Multiple Sclerosis (MS) is 0.35 mg/kg or more. In some examples, the effective dose used to treat, prevent or alleviate Parkinson's Disease is 0.4 mg/kg or more. In some examples, the effective dose used to treat, prevent or alleviate Parkinson's Disease is 0.45 mg/kg or more. In some examples, the effective dose used to treat, prevent or alleviate Parkinson's Disease is 0.5 mg/kg or more. In all cases, the dose described herein is greater than zero mg/kg and less than 5 mg/kg.

In some examples, the effective dose used to treat, prevent or alleviate the symptoms of Alzheimer's is 0.005 mg/kg to 1.0 mg/kg. In some examples, the effective dose used to treat, prevent or alleviate Alzheimer's is 0.01 mg/kg to 0.5 mg/kg. In some examples, the effective dose used to treat, prevent or alleviate Alzheimer's is 0.02 mg/kg to 0.4 mg/kg. In some examples, the effective dose used to treat, prevent or alleviate Alzheimer's is 0.025 mg/kg to 0.4 mg/kg. In some examples, the effective dose used to treat, prevent or alleviate Alzheimer's is 0.025 mg/kg to 0.08 mg/kg. In some examples, the effective dose used to treat, prevent or alleviate Alzheimer's is 0.03 mg/kg to 0.075 mg/kg. In some examples, the effective dose used to treat, prevent or alleviate Alzheimer's is 0.035 mg/kg to 0.4 mg/kg. In some examples, the effective dose used to treat, prevent or alleviate Alzheimer's is 0.035 mg/kg to 0.1 mg/kg. In some examples, the effective dose used to treat, prevent or alleviate Alzheimer's is 0.035 mg/kg to 0.09 mg/kg. In some examples, the effective dose used to treat, prevent or alleviate Alzheimer's is 0.035 mg/kg to 0.08 mg/kg. In some examples, the effective dose used to treat, prevent or alleviate Alzheimer's is 0.035 mg/kg to 0.075 mg/kg. In some examples, the effective dose used to treat, prevent or alleviate Alzheimer's is 0.045 mg/kg to 0.055 mg/kg. In some examples, the effective dose used to treat, prevent or alleviate Alzheimer's is 0.055 mg/kg to 0.085 mg/kg. In some examples, the effective dose used to treat, prevent or alleviate Alzheimer's is 0.055 mg/kg to 0.065 mg/kg. In some examples, the effective dose used to treat, prevent or alleviate Alzheimer's is 0.065 mg/kg to 0.075 mg/kg. In some examples, the effective dose used to treat, prevent or alleviate Alzheimer's is 0.075 mg/kg to 0.1 mg/kg. In some examples, the effective dose used to treat, prevent or alleviate Alzheimer's is 0.07 mg/kg to 0.09 mg/kg. In some examples, the effective dose used to treat, prevent or alleviate Alzheimer's is 0.085 mg/kg to 0.1 mg/kg. In some examples, the effective dose used to treat, prevent or alleviate Alzheimer's is 0.09 mg/kg to 0.2 mg/kg. In some examples, the effective dose used to treat, prevent or alleviate Alzheimer's is 0.1 mg/kg to 0.3 mg/kg. In some examples, the effective dose used to treat, prevent or alleviate Alzheimer's is 0.2 mg/kg to 0.4 mg/kg.

In some examples, the effective dose used to treat, prevent or alleviate the symptoms of Alzheimer's is about 0.005 mg/kg to about 1.0 mg/kg. In some examples, the effective dose used to treat, prevent or alleviate Alzheimer's is about 0.01 mg/kg to about 0.5 mg/kg. In some examples, the effective dose used to treat, prevent or alleviate Alzheimer's is about 0.02 mg/kg to about 0.4 mg/kg. In some examples, the effective dose used to treat, prevent or alleviate Alzheimer's is about 0.025 mg/kg to about 0.4 mg/kg. In some examples, the effective dose used to treat, prevent or alleviate Alzheimer's is about 0.025 mg/kg to about 0.08 mg/kg. In some examples, the effective dose used to treat, prevent or alleviate Alzheimer's is about 0.03 mg/kg to about 0.075 mg/kg. In some examples, the effective dose used to treat, prevent or alleviate Alzheimer's is about 0.035 mg/kg to about 0.4 mg/kg. In some examples, the effective dose used to treat, prevent or alleviate Alzheimer's is about 0.035 mg/kg to about 0.1 mg/kg. In some examples, the effective dose used to treat, prevent or alleviate Alzheimer's is about 0.035 mg/kg to about 0.09 mg/kg. In some examples, the effective dose used to treat, prevent or alleviate Alzheimer's is about 0.035 mg/kg to about 0.08 mg/kg. In some examples, the effective dose used to treat, prevent or alleviate Alzheimer's is about 0.035 mg/kg to about 0.075 mg/kg. In some examples, the effective dose used to treat, prevent or alleviate Alzheimer's is about 0.045 mg/kg to about 0.055 mg/kg. In some examples, the effective dose used to treat, prevent or alleviate Alzheimer's is about 0.055 mg/kg to about 0.085 mg/kg. In some examples, the effective dose used to treat, prevent or alleviate Alzheimer's is about 0.055 mg/kg to about 0.065 mg/kg. In some examples, the effective dose used to treat, prevent or alleviate Alzheimer's is about 0.065 mg/kg to about 0.075 mg/kg. In some examples, the effective dose used to treat, prevent or alleviate Alzheimer's is about 0.075 mg/kg to about 0.1 mg/kg. In some examples, the effective dose used to treat, prevent or alleviate Alzheimer's is about 0.07 mg/kg to about 0.09 mg/kg. In some examples, the effective dose used to treat, prevent or alleviate Alzheimer's is about 0.085 mg/kg to about 0.1 mg/kg. In some examples, the effective dose used to treat, prevent or alleviate Alzheimer's is about 0.09 mg/kg to about 0.2 mg/kg. In some examples, the effective dose used to treat, prevent or alleviate Alzheimer's is about 0.1 mg/kg to about 0.3 mg/kg. In some examples, the effective dose used to treat, prevent or alleviate Alzheimer's is about 0.2 mg/kg to about 0.4 mg/kg.

In some examples, the effective dose used to treat, prevent or alleviate the symptoms of Alzheimer's is 0.001 mg/kg or more. In some examples, the effective dose used to treat, prevent or alleviate the symptoms of Alzheimer's is 0.002 mg/kg or more. In some examples, the effective dose used to treat, prevent or alleviate the symptoms of Alzheimer's is 0.003 mg/kg or more. In some examples, the effective dose used to treat, prevent or alleviate the symptoms of Alzheimer's is 0.004 mg/kg or more. In some examples, the effective dose used to treat, prevent or alleviate the symptoms of Alzheimer's is 0.005 mg/kg or more. In some examples, the effective dose used to treat, prevent or alleviate the symptoms of Alzheimer's is 0.01 mg/kg or more. In some examples, the effective dose used to treat, prevent or alleviate the symptoms of Alzheimer's is 0.025 mg/kg or more. In some examples, the effective dose used to treat, prevent or alleviate the symptoms of Alzheimer's is 0.035 mg/kg or more. In some examples, the effective dose used to treat, prevent or alleviate the symptoms of Alzheimer's is 0.05 mg/kg or more. In some examples, the effective dose used to treat, prevent or alleviate the symptoms of Alzheimer's is 0.075 mg/kg or more. In some examples, the effective dose used to treat, prevent or alleviate the symptoms of Alzheimer's is 0.1 mg/kg or more. In some examples, the effective dose used to treat, prevent or alleviate the symptoms of Alzheimer's is 0.5 mg/kg or less. In some examples, the effective dose used to treat, prevent or alleviate the symptoms of Alzheimer's is 0.35 mg/kg or less. In some examples, the effective dose used to treat, prevent or alleviate the symptoms of Alzheimer's is 0.25 mg/kg or less. In some examples, the effective dose used to treat, prevent or alleviate the symptoms of Alzheimer's is 0.1 mg/kg or less. In some examples, the effective dose used to treat, prevent or alleviate the symptoms of Alzheimer's is 0.075 mg/kg or less. In some examples, the effective dose used to treat, prevent or alleviate the symptoms of Alzheimer's is 0.05 mg/kg or less. In all cases, the dose described herein is greater than zero mg/kg and less than 5 mg/kg.

In some examples, the invention is a method of treating any of these diseases, or of treating neuromuscular, neurodegenerative, autoimmune, developmental, metabolic, or any disorder related to aging, comprising administering to a patient in need of treatment of a traumatic CNS injury or neurodegenerative disease an effective dose of DNP, or a pharmaceutically acceptable salt thereof, over a period sufficiently long to achieve remission of the symptoms of the disease, wherein the effective dose of the DNP is continued in the dose range of 0.001 mg/kg of body weight to 5 mg/kg of body weight to induce BDNF expression in brain. Indeed, the invention comprises administration of DNP, wherein the dose of DNP is useful to prevent harm in humans, as a means to avoid inducing too much BDNF, or have no effect by inducing too little BDNF. As is also apparent from the disclosures herein, the invention also comprises enhancing expression of BDNF, which provides protection from muscle wasting or muscle dysfunction, since BDNF is expressed not only in brain, but in muscle and may act as a myokine.

In some examples, the invention is a method of treating neuromuscular or neurodegenerative or autoimmune or developmental or metabolic disorders, comprising receiving an effective dose of DNP, or a pharmaceutically acceptable salt thereof, over period sufficiently long to achieve remission of the symptoms of the disease, wherein the effective dose of the DNP is continued to be received in the dose range of 0.001 mg/kg of body weight to 5 mg/kg of body weight to increase BDNF to attenuate disease progression or provide remission of symptoms. In some examples, the invention is a method of treating neuromuscular or neurodegenerative or autoimmune or developmental or metabolic disorders, comprising providing instructions to administer an effective dose DNP, or a pharmaceutically acceptable salt thereof, over period sufficiently long to achieve remission of the symptoms of the disease, wherein the effective dose of the DNP is instructed to be received in the dose range of 0.001 mg/kg of body weight to 5 mg/kg of body weight.

In some examples, the invention is a method of treating any of the diseases identified herein, whereby the effective dose of DNP has a lasting effect on sustaining elevated levels of BDNF for up to three weeks after the last dose of DNP is received. In some examples, the invention is a method of treating any of the diseases identified herein, whereby the effective dose of DNP has a lasting effect on sustaining elevated levels of BDNF for up to two weeks after the last dose of DNP is received. In some examples, the invention is a method of treating any of the diseases identified herein, whereby the effective dose of DNP has a lasting effect on sustaining elevated levels of BDNF for up to one week after the last dose of DNP is received. In some examples, the invention is a method of treating any of the diseases identified herein, whereby the effective dose of DNP has a lasting effect on sustaining elevated levels of BDNF for up to three days after the last dose of DNP is received. In some examples, the invention is a method of treating any of the diseases identified herein, whereby the effective dose of DNP has a lasting effect on sustaining elevated levels of BDNF for up to two days after the last dose of DNP is received. In some examples, the invention is a method of treating any of the diseases identified herein, whereby the effective dose of DNP has a lasting effect on sustaining elevated levels of BDNF for up to one day after the last dose of DNP is received.

In an embodiment, a dose encompassed herein may be administered as a composition based on the weight of the subject. In an embodiment, a dose may be administered per unit weight of the subject (e.g., mg of a composition described herein per kg weight of subject). In an embodiment, a dose encompassed herein may be administered as a composition based solely on the weight of the dose, without regard to the weight of the subject (e.g., mg of a composition described herein per dose administered to subject). In an embodiment, the dose is determined based on the weight of the active ingredients in the carrier. In another embodiment, the dose is determined based on the total weight of the active ingredients of the composition in the carrier. We are presuming in our dose range, that the average adult patient weights approximately 60 kg.

Composition

In some embodiments, a pharmaceutical composition includes DNP, or a pharmaceutically acceptable salt, solvate, or hydrate thereof, comprising an effective dose of DNP, wherein the effective dose of the DNP is in the range of 0.001 mg/kg of body weight to 5 mg/kg of body weight; 0.01 mg/kg to 1 mg/kg; 0.01 mg/kg to 0.1 mg/kg; 0.1 mg/kg to 0.5 mg/kg; or 1 mg/kg to 5 mg/kg. In some embodiments, the pharmaceutical composition is an effective dose to induce BDNF expression to reverse, slow or prevent neuromuscular and/or neurodegeneration and/or muscle wasting.

In some embodiments, a pharmaceutical composition includes DNP, or a pharmaceutically acceptable salt, solvate, or hydrate thereof, comprising an effective dose of DNP, wherein the effective dose of the DNP is in the range of about 0.001 mg/kg of body weight to about 5 mg/kg of body weight; about 0.01 mg/kg to about 1 mg/kg; about 0.01 mg/kg to about 0.1 mg/kg; about 0.1 mg/kg; about 0.1 mg/kg to about 0.5 mg/kg; about 0.5 mg/kg; about 1 mg/kg; about 1 mg/kg to about 5 mg/kg; about 5 mg/kg. In some embodiments, the pharmaceutical composition is an effective dose to induce BDNF expression to reverse, slow or prevent neuromuscular and/or neurodegeneration and/or muscle wasting.

In some embodiments, the pharmaceutical composition is an immediate release formation. In some embodiments, the pharmaceutical composition is rapidly dissolving. In some embodiments, the pharmaceutical composition is a sustained release formation. In some embodiments, the pharmaceutical composition is a controlled release formation.

In other embodiments, as set forth in greater detail elsewhere herein, the dosage and dosing regimen for the active ingredients may be optimized based on the health and condition of the subject to be treated, as well as the desired outcome of the treatment.

Unit Dose

In some embodiments, a pharmaceutical composition includes DNP, or a pharmaceutically acceptable salt, solvate, or hydrate thereof, comprising a unit dose, wherein the unit dose is in the range of about 0.1 mg to about 300 mg; wherein the unit dose is in the range of about 0.1 mg to about 1 mg; wherein the unit dose is in the range of about 1 mg to about 5 mg; wherein the unit dose is about 1 mg; wherein the unit dose is about 2 mg; wherein the unit dose is about 3 mg; wherein the unit dose is about 4 mg; wherein the unit dose is about 5 mg; wherein the unit dose is the range of about 5 mg to about 10 mg; wherein the unit dose is about 6 mg; wherein the unit dose is about 7 mg; wherein the unit dose is about 8 mg; wherein the unit dose is about 9 mg; wherein the unit dose is about 10 mg; wherein the unit dose is the range of about 10 mg to about 15 mg; wherein the unit dose is about 11 mg; wherein the unit dose is about 12 mg; wherein the unit dose is about 13 mg; wherein the unit dose is about 14 mg; wherein the unit dose is about 15 mg; wherein the unit dose is the range of about 15 mg to about 20 mg; wherein the unit dose is about 16 mg; wherein the unit dose is about 17 mg; wherein the unit dose is about 18 mg; wherein the unit dose is about 19 mg; wherein the unit dose is about 20 mg; wherein the unit dose is the range of about 20 mg to about 30 mg; wherein the unit dose is about 25 mg; wherein the unit dose is about 30 mg; wherein the unit dose is the range of about 30 mg to about 40 mg; wherein the unit dose is about 35 mg; wherein the unit dose is about 40 mg; wherein the unit dose is the range of about 40 mg to about 50 mg; wherein the unit dose is about 45 mg; wherein the unit dose is about 50 mg; wherein the unit dose is the range of about 50 mg to about 100 mg; wherein the unit dose is about 75 mg; wherein the unit dose is about 100 mg; wherein the unit dose is the range of about 100 mg to about 200 mg; wherein the unit dose is about 150 mg; wherein the unit dose is about 200 mg; wherein the unit dose is the range of about 200 mg to about 300 mg; wherein the unit dose is about 200 mg; wherein the unit dose is about 250 mg; or wherein the unit dose is about 300 mg.

In some embodiments, a pharmaceutical composition includes DNP, or a pharmaceutically acceptable salt, solvate, or hydrate thereof, comprising a unit dose, wherein the unit dose is in the range of 0.1 mg to 300 mg; wherein the unit dose is in the range of 0.1 mg to 1 mg; wherein the unit dose is in the range of 1 mg to 5 mg; wherein the unit dose is 1 mg; wherein the unit dose is 2 mg; wherein the unit dose is 3 mg; wherein the unit dose is 4 mg; wherein the unit dose is 5 mg; wherein the unit dose is the range of 5 mg to 10 mg; wherein the unit dose is 6 mg; wherein the unit dose is 7 mg; wherein the unit dose is 8 mg; wherein the unit dose is 9 mg; wherein the unit dose is 10 mg; wherein the unit dose is the range of 10 mg to 15 mg; wherein the unit dose is 11 mg; wherein the unit dose is 12 mg; wherein the unit dose is 13 mg; wherein the unit dose is 14 mg; wherein the unit dose is 15 mg; wherein the unit dose is the range of 15 mg to 20 mg; wherein the unit dose is 16 mg; wherein the unit dose is 17 mg; wherein the unit dose is 18 mg; wherein the unit dose is 19 mg; wherein the unit dose is 20 mg; wherein the unit dose is the range of 20 mg to 30 mg; wherein the unit dose is 25 mg; wherein the unit dose is 30 mg; wherein the unit dose is the range of 30 mg to 40 mg; wherein the unit dose is 35 mg; wherein the unit dose is 40 mg; wherein the unit dose is the range of 40 mg to 50 mg; wherein the unit dose is 45 mg; wherein the unit dose is 50 mg; wherein the unit dose is the range of 50 mg to 100 mg; wherein the unit dose is 75 mg; wherein the unit dose is 100 mg; wherein the unit dose is the range of 100 mg to 200 mg; wherein the unit dose is 150 mg; wherein the unit dose is 200 mg; wherein the unit dose is the range of 200 mg to 300 mg; wherein the unit dose is 200 mg; wherein the unit dose is 250 mg; or wherein the unit dose is 300 mg.

In some embodiments, a pharmaceutical composition includes DNP, or a pharmaceutically acceptable salt, solvate, or hydrate thereof, comprising a unit dose, wherein the unit dose is in the range of 0.1 mg or more; wherein the unit dose is in the range of 0.5 mg or more; wherein the unit dose is in the range of 1 mg or more; wherein the unit dose is 5 mg or more; wherein the unit dose is 10 mg or more; wherein the unit dose is 15 mg or more; wherein the unit dose is 20 mg or more; wherein the unit dose is 30 mg or more; wherein the unit dose is 40 mg or more; wherein the unit dose is 50 mg or more; wherein the unit dose is 100 mg or more; wherein the unit dose is 150 mg or more; wherein the unit dose is 200 mg or more; or wherein the unit dose is 250 mg or more, but in all cases not greater than 300 mg.

In some embodiments, a pharmaceutical composition includes DNP, or a pharmaceutically acceptable salt, solvate, or hydrate thereof, comprising a unit dose, wherein the unit dose is 0.25 mg or less, but in all cases greater than zero; wherein the unit dose is 0.5 mg or less; wherein the unit dose is 1 mg or less; wherein the unit dose is 5 mg or less; wherein the unit dose is 10 mg or less; wherein the unit dose is 15 mg or less; wherein the unit dose is 20 mg or less; wherein the unit dose is 30 mg or less; wherein the unit dose is 40 mg or less; wherein the unit dose is 50 mg or less; wherein the unit dose is 100 mg or less; wherein the unit dose is 150 mg or less; wherein the unit dose is 200 mg or less; wherein the unit dose is 250 mg or less; or wherein the unit dose is 300 mg or less.

In some embodiments, the unit dose is an immediate release formation. In some embodiments, the unit dose is an extended release formation. In some embodiments, the unit dose is a sustained release formation. In some embodiments, the unit dose is a controlled release formation. In some embodiments, the unit dose is an oral dosage form. In some embodiments, the oral dosage form is a tablet. In some embodiments, the oral dosage form is a capsule. In some embodiments, the unit dose is a capsule with no filler. In some embodiments, the oral dosage form is rapidly dissolving.

In some embodiments, the unit dose is delivered intravenously. In some embodiments, the unit dose is delivered by means of an intravenous drip along with saline. In some embodiments, the unit dose is delivered by means of an intravenous drip along with saline, other medications, vitamins and/or nourishment. In some embodiments, the unit dose is delivered subcutaneously. In some embodiments, the unit dose is delivered topically. In some embodiments, the unit dose is delivered transdermally. In some embodiments, the unit dose is in the form of a patch.

In some embodiments, the unit dose is an effective amount to induce BDNF expression to reverse, slow or prevent neuromuscular and/or neurodegeneration and/or muscle wasting. In some embodiments, the unit dose is a treatment for Huntington's disease. In some embodiments, the unit dose is a treatment for Multiple Sclerosis (MS). In some embodiments, the unit dose is a treatment for Epilepsy. In some embodiments, the unit dose is a treatment for Parkinson's Disease. In some embodiments, the unit dose is a treatment for Alzheimer's. In some embodiments, the unit dose is a treatment for Rhett Syndrome. In some embodiments, the unit dose is a treatment for, but not limited to, Traumatic Brain Injury (TBI), Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity onset diabetes of the young (MODY: MODY1, MODY2, MODY3, MODY4, MODY5, MODY6, MODY7, MODY8, MODY9, MODY10, MODY11)), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD)), Becker, Myotonic, Congenital, Emery-Dreifuss, Facioscapulohumeral, Limb-girdle, Distal, and Oculopharyngeal), severe burns, aging, Amyotrophic Lateral Sclerosis (ALS), Ataxia (Friedreich's Ataxia, Spinocerebellar ataxias 1 (SCA1), Spinocerebellar ataxias 2 (SCA2), Spinocerebellar ataxias 3 (SCA3), Spinocerebellar ataxias 6 (SCA6), Spinocerebellar ataxias 7 (SCA7), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), mitochondrial diseases, developmental disorders, metabolic syndrome (increased blood pressure, high blood sugar level, excess body fat around the waist and abnormal cholesterol levels) and/or autoimmune disorders.

The dose may be administered as a single daily dose, a twice-daily dose, three times daily, or more frequently. The dose may be administered three times weekly, twice weekly, once weekly, or less frequently. In an embodiment, administration frequency may be between 1 and 5 times a day. In another embodiment, administration frequency may be between 2 and 4 times a day. In another embodiment, administration frequency may be at least 3 times a day. In another embodiment, administration frequency may be twice a day. In another embodiment, administration frequency may be once a day. In another embodiment, administration frequency may be less frequent than once a day. In other embodiments, administration frequency may be once every 2 days or once every 3 days or once every 4 days or once every 5 days or once every 6 days. In another embodiment, administration frequency may be once a week. In another embodiment, administration frequency may change with time, starting at a certain rate, such as once or twice a day, and then decreasing to less frequently, such as once every 2 days or once every 3 days, or once a week, after the first day of treatment. In another embodiment, administration frequency may change with time, starting at a certain rate, such as once or twice a day, and then decreasing to less frequently, such as once every 2 days or once every 3 days, or once a week, after the first two or three days of treatment. In another embodiment, administration frequency may change with time, starting at a certain rate, such as once or twice a day, and then decreasing to less frequently, such as once every 2 days or once every 3 days, or once a week, after the first week of treatment. In another embodiment, administration frequency may be on demand, as therapeutic treatment is required or desired.

Since the study in the EAE model for MS showed that after 2 weeks of DNP treatment, there is a statistically elevated level of BDNF protein 3-weeks post treatment (FIG. 2b), dose frequency could be chronic to raise BDNF protein levels, followed by infrequent doses or "drug holidays". Infrequent doses would be used as maintenance doses to keep BDNF at elevated levels. Therefore, after an initial period of higher frequency doses, frequency of doses could then be reduced to once every week, once every two weeks, once every three weeks or once a month.

It will be understood, based on the disclosure encompassed herein, how to determine whether a subject needs an additional and/or continued dose. It will also be understood that the selected dosing frequency may require an adjustment of the dosage of active ingredient. It will also be understood, based on the disclosure encompassed herein, that the selected dosage of active ingredient may require an adjustment of the dosing frequency. The disclosure encompassed herein, in combination with the skill in the art, will enable the skilled artisan to optimize both the dosage of the active ingredient and the frequency of administration of the active ingredient to treat a subject in need thereof.

The unit dose may also be adjusted based upon the size of the patient. The numbers provided herein are based upon a 60 kg patient. The same therapy could be provided for a smaller or larger sized patient, but reducing or increasing the dose size. By way of example only, a 20 kg child would need a much smaller dose.

Co-Administration of Compositions

In an embodiment, a composition described herein is administered in conjunction with one or more other medications or consumer products. Such other medications or consumer products may be administered or co-administered in forms and dosages as known in the art, or in the alternative, as has been described above for administration of active ingredients using the compositions described herein. By way of example only, for stroke patients, DNP may be administered along with Tissue plasminogen activator (tPA).

For Diabetes Mellitus, DNP may be administered along with insulin (Humulin N, Novolin N) or other biologics as an injectable, or as an oral tablet with Metformin (Glucophage, Glumetza, others), sulfonylureas (glyburide (DiaBeta, Glynase), glipizide (Glucotrol) and glimepiride (Amaryl), etc.), Meglitinides (epaglinide (Prandin) and nateglinide (Starlix)), Thiazolidinediones (Rosiglitazone (Avandia) and pioglitazone (Actos)), DPP-4 inhibitors (sitagliptin (Januvia), saxagliptin (Onglyza) and linagliptin (Tradjenta)), GLP-1 receptor agonists ((Byetta) and liraglutide (Victoza)), SGLT2 inhibitors (canagliflozin (Invokana) and/or dapagliflozin (Farxiga)).

For Huntington's Disease, DNP may be administered with Tetrabenazine (Xenazine), Antipsychotic drugs, such as haloperidol (Haldol), or others like amantadine, levetiracetam (Keppra) and/or clonazepam (Klonopin).

For Parkinson's Disease, DNP may be administered with Carbidopa-levodopa (Rytary, Sinemet), Dopamine agonists such as pramipexole (Mirapex), ropinirole (Requip) and rotigotine (given as a patch, Neupro), a short-acting injectable dopamine agonist, apomorphine (Apokyn), MAO-B inhibitors (Eldepryl, Zelapar), or Catechol-O-methyltransferase (COMT) inhibitors (Entacapone (Comtan), Tolcapone (Tasmar), etc.), Anticholinergics (benztropine (Cogentin), trihexyphenidyl), and/or Amantadine.

For Alzheimer's Disease, DNP may be administered with Cholinesterase inhibitors (donepezil (Aricept), galantamine (Razadyne) and rivastigmine (Exelon)), and/or Memantine (Namenda).

For Depression, DNP may be administered with selective serotonin reuptake inhibitors (SSRIs) (luoxetine (Prozac), paroxetine (Paxil, Pexeva), sertraline (Zoloft), citalopram (Celexa) and escitalopram (Lexapro)), Norepinephrine-dopamine reuptake inhibitors (NDRIs). Bupropion (Wellbutrin, Aplenzin, Forfivo XL), atypical antidepressants (Trazodone, mirtazapine (Remeron), vortioxetine (Brintellix), vilazodone (Viibryd), etc.), and/or tricyclic antidepressants (imipramine (Tofranil), nortriptyline (Pamelor), Monoamine oxidase inhibitors (MAOIs) tranylcypromine (Parnate), phenelzine (Nardil), isocarboxazid (Marplan), etc.).

For Schizophrenia, DNP may also be administered along with Atypical antipsychotics (Aripiprazole (Abilify), Asenapine (Saphris), Clozapine (Clozaril), Iloperidone (Fanapt), etc.), Conventional, or typical, and/or antipsychotics (Chlorpromazine, Fluphenazine, Haloperidol (Haldol), Perphenazine, etc.).

For MS, DNP may be administered along with Corticosteroids (prednisone, intravenous methylprednisolone), Beta interferons, Glatiramer acetate (Copaxone), Dimethyl fumarate (Tecfidera), Fingolimod (Gilenya), Teriflunomide (Aubagio), Natalizumab (Tysabri), Alemtuzumab (Lemtrada), and/or Mitoxantrone, etc.

For epilepsy, DNP may be administered along with Carbamazepine, clobazam, clonazepam, eslicarbazepine, ethosuximide, gabapentin, lacosamide, lamotrigine, levetiracetam, oxcarbazepine, perampanel, phenobarbital, phenytoin, pregabalin, primidone, retigabine, rufinamide, sodium valproate, tiagabine, topiramate, vigabatrin, and/or zonisamide, etc.

For Traumatic Brain Injury (TBI), DNP may be administered along with Diuretics, anti-seizure drugs, and/or Coma-inducing drugs.

For Lupus, DNP may be administered along with Nonsteroidal anti-inflammatory drugs (NSAIDs) (naproxen sodium (Aleve) and ibuprofen (Advil, Motrin IB, others)), Antimalarial drugs such as hydroxychloroquine (Plaquenil), Corticosteroids (Prednisone, etc.), and/or Immunosuppressants (azathioprine (Imuran, Azasan), mycophenolate (CellCept), leflunomide (Arava), methotrexate (Trexall), etc.).

For Prader Willi Syndrome, DNP may be administered along with Human growth hormone (HGH), and/or sex hormone treatment (testosterone for males or estrogen and progesterone for females), etc.

For Graves' disease, DNP may be administered along with Anti-thyroid medications (propylthiouracil and methimazole (Tapazole)), and/or Beta blockers (Propranolol (Inderal), Atenolol (Tenormin), Metoprolol (Lopressor, ToprolXL), Nadolol (Corgard)).

For Muscular Dystrophy, DNP may be administered along with Corticosteroids, such as prednisone and/or Heart medications, such as angiotensin-converting enzyme (ACE) inhibitors or beta blockers.

DNP may also be administered along with pain relief medication, vitamins, nutrition, hydration fluids, or other medication.

The term "co-administration" or "combination therapy" is used to describe a therapy in which at least two compositions, which may include one or more product compositions as described herein, are used to treat, address, or affect a skin condition or another disorder as described herein at the same time. In an embodiment, at least two compositions in effective amounts are used to treat, address, or affect a skin condition or another disorder as described herein at the same time. In another embodiment, at least two active ingredients, the combination of which comprises an effective amount, are used to treat, address, or affect a skin condition or another disorder as described herein at the same time. In an embodiment, the result of treatment with the at least two compositions may be additive of the treatment results obtained using each composition separately, either directly additive, or additive to a degree lesser than the results obtained with the two compositions separately. In an embodiment, the result of treatment with the at least two compositions may be synergistic, to varying degrees. In an embodiment, the result of treatment with the at least two compositions may be greater than the treatment results obtained using each composition separately. In an aspect, the result of treatment for at least two active ingredients is less than that obtained with the active ingredients separately, while the other active ingredients in the composition are about the same as the results of treatment obtained separately. In an aspect, the result of treatment for all active ingredients in the composition is less than that obtained with the active ingredients separately.

Although the term co-administration encompasses the administration of two compositions to the patient at the same time, it is not necessary that the compositions be administered to the patient at the same time, although effective amounts of the individual active ingredients delivered by the compositions will be present in the patient at the same time.

A product composition described herein may advantageously be administered in combination with at least one other therapeutic agent to provide improved treatment of a skin condition or another disorder. The combinations, uses and methods of treatment of the invention may also provide advantages in treatment of patients or consumers who fail to respond adequately to other known treatments. In an embodiment, a product composition described herein may be administered to a patient already undergoing treatment with at least one other skin care composition, to provide improved treatment of any combination of conditions described herein. In an embodiment, a product composition set forth herein is co-administered with one or more lotions, foams, or creams.

It will further be understood by the skilled artisan that, in addition to the above embodiments of dosage and dosing regimens, both the dosage and the dosing regimen will be considered and each adjusted, as necessary, in view of the condition of the subject being treated.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined.

Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method of treating a disease or disorder selected from Amyotrophic Lateral Sclerosis (ALS), Atypical Parkinsonism, and an Autism Spectrum Disorder (ASD), comprising administering to a patient in need of treatment a pharmaceutical composition of 2,4-dinitrophenol (DNP), or a pharmaceutically acceptable salt, solvate, or hydrate thereof, comprising an effective dose of 2,4-dinitrophenol (DNP), wherein the effective dose of the 2,4-dinitrophenol (DNP) is in the range of about 0.001 mg/kg of body weight to about 5 mg/kg of body weight.

2. The method of claim 1, wherein the disease or disorder is Amyotrophic Lateral Sclerosis (ALS).

3. The method of claim 1, wherein the disease or disorder is Atypical Parkinsonism.

4. The method of claim 3, wherein the Atypical Parkinsonism is selected from progressive supranuclear palsy (PSP), dementia with Lewy bodies, multiple system atrophy, and corticobasal degeneration (CBD).

5. The method of claim 1, wherein the disease or disorder is an Autism Spectrum Disorder (ASD).

6. The method of claim 5, wherein the Autism Spectrum Disorder is selected from Asperger's Syndrome, Pervasive Developmental Disorders (PDDs), Childhood Disintegrative Disorder (CDD), and Autistic disorder.

7. The method of claim 1, wherein the effective dose of 2,4-dinitrophenol (DNP) is in the range of about 0.001 mg/kg to about 0.01 mg/kg.

8. The method of claim 1, wherein the effective dose of 2,4-dinitrophenol (DNP) is in the range of about 0.01 mg/kg to about 0.1 mg/kg.

9. The method of claim 1, wherein the effective dose of 2,4-dinitrophenol (DNP) is in the range of about 0.1 mg/kg to about 1 mg/kg.

10. The method of claim 1, wherein the effective dose of 2,4-dinitrophenol (DNP) is in the range of about 1 mg/kg to about 5 mg/kg.

11. A method of treating a disease or disorder selected from Amyotrophic Lateral Sclerosis (ALS), Atypical Parkinsonism, and an Autism Spectrum Disorder (ASD), comprising administering to a patient in need of treatment a pharmaceutical composition of 2,4-dinitrophenol (DNP), or a pharmaceutically acceptable salt, solvate, or hydrate thereof, comprising a 2,4-dinitrophenol (DNP) unit dose, wherein the unit dose is in the range of about 0.1 mg to about 300 mg.

12. The method of claim 11, wherein the disease or disorder is Amyotrophic Lateral Sclerosis (ALS).

13. The method of claim 11, wherein the disease or disorder is Atypical Parkinsonism.

14. The method of claim 13, wherein the Atypical Parkinsonism is selected from progressive supranuclear palsy (PSP), dementia with Lewy bodies, multiple system atrophy, and corticobasal degeneration (CBD).

15. The method of claim 11, wherein the disease or disorder is an Autism Spectrum Disorder (ASD).

16. The method of claim 15, wherein the Autism Spectrum Disorder is selected from Asperger's Syndrome, Pervasive Developmental Disorders (PDDs), Childhood Disintegrative Disorder (CDD), and Autistic disorder.

17. The method of claim 11, wherein the unit dose is in the range of about 0.1 mg to about 1 mg.

18. The method of claim 11, wherein the unit dose is in the range of about 1 mg to about 5 mg.

19. The method of claim 11, wherein the unit dose is in a range selected from about 5 mg to about 10 mg, about 10 mg to about 15 mg, about 15 mg to about 20 mg, about 20 mg to about 30 mg, about 30 mg to about 40 mg, and about 40 mg to about 50 mg.

20. The method of claim 11, wherein the unit dose is in the range from about 50 mg to about 100 mg.

21. The method of claim 11, wherein the unit dose is in the range from about 100 mg to about 200 mg.

22. The method of claim 11, wherein the unit dose is in the range from about 200 mg to about 300 mg.

23. A method of treating a disease or disorder selected from Amyotrophic Lateral Sclerosis (ALS), Atypical Parkinsonism, and an Autism Spectrum Disorder (ASD), comprising:
receiving a pharmaceutical composition of 2,4-dinitrophenol (DNP), or a pharmaceutically acceptable salt, solvate, or hydrate thereof, comprising an effective dose of 2,4-dinitrophenol (DNP), or
providing instructions to administer a pharmaceutical composition of 2,4-dinitrophenol (DNP), or a pharmaceutically acceptable salt, solvate, or hydrate thereof, comprising an effective dose of 2,4-dinitrophenol (DNP),
wherein the effective dose of the 2,4-dinitrophenol (DNP) is in the range of about 0.001 mg/kg of body weight to about 5 mg/kg of body weight.

* * * * *